United States Patent [19]
Schofield et al.

[11] Patent Number: 5,484,718
[45] Date of Patent: Jan. 16, 1996

[54] NODULATION GENE PROMOTER

[75] Inventors: Peter R. Schofield, San Francisco, Calif.; John M. Watson, Holder, Australia; Kieran F. Scott, Page, Australia; Barry G. Rolfe, Curtin, Australia; Michael A. Djordjevic, Aranda, Australia; Peter L. Kuempel; Roger W. Innes, both of Boulder, Colo.

[73] Assignee: Mycogen Plant Science, Inc., San Diego, Calif.

[21] Appl. No.: 875,300

[22] Filed: Jun. 17, 1986

[51] Int. Cl.$^6$ .......................... C12N 15/31; C12N 15/32; C12N 15/74
[52] U.S. Cl. .................. 435/172.3; 435/69.1; 435/71.1; 435/252.2; 435/878; 536/24.1
[58] Field of Search .................................. 435/172.3, 68, 435/317, 320, 69.1, 320.1, 71.1, 252.2, 878; 536/27, 24.1; 935/29, 30, 41, 56

[56] References Cited

U.S. PATENT DOCUMENTS 4,448,885  5/1984  Schnepf et al. ........................ 935/29

OTHER PUBLICATIONS

Kaluza et al., 1985. FEBS Letters 188(1):37–42.
Marvel et al. 1985. Proc. Natl. Acad. Sci. USA 82:5841–5845.
Russell et al. 1985. J. Bacteriol. 164:1301–1308.
Downie et al (1983) "Cloned Nodulation Genes . . . " Mol Gen Genet 190:359–65.
Olson et al (1985) "Identification of Genes . . . " Bio Technology Feb. 143–149.
Rostas et al., (1986) Proc. Natl. Acad. Sci. USA, vol. 83, pp. 1757–1761.
Gerhold et al. (1989) Plant Molecular Biology, 12:181–188.
Fisher et al. (1988) Genes & Development, 2:282–293.
Fisher et al. (1987) Genetics 117:191–201.
Fisher et al. (1989) Journal of Bacteriology, 171(10):5492–5502.
Hong et al. (1987) Nucleic Acids Research, 15(23):9677–9690.
Rostas et al. (1986) Proc. Natl. Acad. Sci. USA 83:1757–1761.
Schofield, Ph.D. Thesis (1984) Australian National University, Canberra, Australia, Chapters 1–7 and 9.
K. F. Scott (1985) in *Nitrogen Fixation Research Progress*, Evans et al. (eds.), Martinus–Nijhoff Publishers, Dordrecht, The Netherlands, p. 130.
Kondorosi et al. (1985) ibid., pp. 73–78.
Long et al. (1985) ibid., pp. 87–93.
Downie et al. (1985) ibid., pp. 95–100.
Innes et al. (1985) Mol. Gen. Genet. 201:426–432.
Eglehoff et al. DNA 4:241–248 (1985).
Jacobs et al., (1985) J. Bacteriol. 162:469–476.
Rossen et al. (1984) Nucleic Acids Research 12:9497–9508.
Torok et al. (1984) Nucleic Acids Research 12:9509–9524.

(List continued on next page.)

*Primary Examiner*—David T. Fox
*Attorney, Agent, or Firm*—Saliwanchik & Saliwanchik

[57] ABSTRACT

The invention includes a consensus nucleotide sequence found in the promoter regions of those Rhizobium and Bradyrhizobium nodulation genes which are activated by chemical inducer(s) in legume exudate. A promoter comprising the consensus sequence is a legume exudate-inducible promoter. A recombinant gene comprising a structural gene and a legume exudate-inducible promoter is selectively expressed in the presence of legume exudate or chemical inducer(s) and a functional nodD gene. The consensus nucleotide sequence is ATCCAYNNYGYRGATGNWYKYKATC-SAAWCAATCRATTTTACCARWYYKNSRR where N is A, G, C or T
Y is C or T
R is A or G
W is A or T
K is G or T and
S is C or G.

24 Claims, 16 Drawing Sheets

```
R. trifolii
nodABC    5'... CGCATTC-TCGATCCACGCTGTAGATGATTGCGATCCAAACAATCAATTTTACCAATCTTTCGGAGTGCTTATTAG ... 3'

R. trifolii
nodFE     5'... CTCATTCCTTCATCCATACTGCGGATGCTTTCGATCCAATCAATCAATTTTACCAATCCTTCGGCATGCTCCATAG ... 3'

R. meliloti
nodABC    5'... GCATGTGCGGCATCCATATCGCAGATGATCGTTATCCAAACAATCAATTTTACCAATCTTGCAGACT-CCTATTAG ... 3'

B. parasponia
nodKABC   5'... GTTGTGAGTCTATCCATCGTGTGGATGTATTCTATCGAAACAATCGATTTTACCAGATTGCGGAATGTTGGATAGC ... 3'

Consensus
          5'... ATCCAYNNYGYRGATGNWYKYKATCSAAWCAATCRATTTTACCARWYYKNSRR ... 3' where R = A or G
      W = A or T
      S = C or G
      Y = C or T
      K = G or T
      N = A or G or C or T
```

OTHER PUBLICATIONS

Rolfe et al. (1985) *Nitrogen Fixation Research Progress* Evans et al. (eds.) Martinius Nijhoff pp. 79–85.
Schofield and Watson (1985) ibid p. 125.
Schofield and Watson (1986) Nucleic Acids Research 14:2.
Scott (1986) Nucleic Acids Research 14:2905–2919.
Mulligan and Long (1985) Proc. Natl. Acad. Sci. USA 82:6609–6613.
Rossen et al. (1985) EMBO J. 4:3369–3373.
Shearman et al. (1986) EMBO J. 5:647–652.
Schofield et al. (1983) Mol. Gen. Genet. 192:459–465.
Djordjevic et al. (1985) Mol. Gen. Genet. 200:463–471.

2950
3000
3050
3100
3150
3200
3250
3300 nodF

```
CCGCATCTATTTGGAAAGAAATGCGGAAGGCCCGGTCCGCAATCAGCCC   3650
GGCGTAGATAAACCTTTCTTTACGCCTTCCGGGCAGGCGGTTAGTCGGG
 A   S   I   W   K   E   M   R   E   G   P   S   A   I   S   P

ATCATCACGACAGATCT
TAGTAGTGCTGTCTAGA
 I   I   T   T   D   L
```

Fig. 3

```
       M
5'...CATGTGTGAGTCTATCCATCGTGTGGATGTATTCTATCGAAACAATCGATTTACCAGATTGCGGAATGTT
3'...GTACACACTCAGATAGGTAGCACACCTACATAAGATAGCTTTGTTAGCTAAAATGGTCTAACGCCTTACAA
      nodD GGATAGCAAACATCAGTTTGGAAAATAAATTAGGCATACCACGATGGCTGCTGGTCGTACGCGGGCTCCGAG
CCTATCGTTTGTAGTCAAACCTTTTATTTAATCCGTATGGTGCTACCGACGACCAGCATGCGCCCGAGGCTC AAAGACTCCTGGGGACGTGCAAGCACCCGCCGAATCAGTTTGGGAAACGGATATCGCTGCCGCATGCGAATT
TTTCTGAGGACCCCTGCACGTTCGTGGGCGGCTTAGTCAAACCCTTTGCCTATAGCGACGGCGTACGCTTAA GCGCCTCTTCCGGTGCGACGAGCACGCGATGTGACGCTAGGAAGCCCCGATAAACCTTCGTATGGCGTGTT
CGCGGAGAAGGCCACGCTGCTCGTGCGCTACACTGCGATCCTTCGGGGCTATTTGGAAGCATACGCACAA CCAACCCTTTCCATATCGGCGGTTTACCCGCGTACACTTGAGAGCGTGCTCAGCCTCACCTTAGTGTCGCGA
GGTTGGGAAAGGTATAGCCGCCAAATGGGCGCATGTGAACTCTCGCACGAGTCGGAGTGGAATCACAGCGCT M
CCAAGCGGCGTGCGCAGATTGCGGATGCCAAATATCTCCGGCGACTGGCCAAATG...3'
GGTTCGCCGCACGCGTCTAACGCCTACGGTTTATAGAGGCCGCTGACCGGTTTAC...5'
                                                      nodKABC
```

Fig. 4

R. trifolii
nodABC    5'... CGCATTC-TCGATCCACGCTGTAGATGATTGCGATCCAAACAATCAATTTACCAATCTTTCGGAGTGCTTATTAG ... 3'

R. trifolii
nodFE     5'... CTCATTCCTTCATCCATACTGCGGATGCTTTCGATCAATCAATTTACCAATCCTTCGGCATGCTCCATAG ... 3'

R. meliloti
nodABC    5'... GCATGTGCGGGCATCCATATCGCAGATGATCGTTATCCAAACAATCAATTTACCAATCTTGCAGACT-CCTATTAG ... 3'

B. parasponia
nodKABC   5'... GTTGTGAGTCTATCCATCGTGTGGATGTATTCTATCGAAACAATCGATTTTACCAGATTGCGGAATGTTGGATAGC ... 3'

Consensus
          5'... ATCCAYNNYGYRGATGNWYKYKATCSAAWCAATCRATTTTACCARWYYKNSRR ... 3' where  R = A or G
       W = A or T
       S = C or G
       Y = C or T
       K = G or T
       N = A or G or C or T

NODULATION GENE PROMOTER

FIELD OF THE INVENTION

The present invention relates in general to the molecular genetics of the legume-Rhizobium symbiosis, and in particular to the isolation and identification of regulatory sequences of nodulation gene promoters.

BACKGROUND OF THE INVENTION

Soil bacteria of the genus Rhizobium, a member of the family Rhizobiaceae, are capable of infecting plants and inducing a highly differentiated structure, the root nodule, within which atmospheric nitrogen is reduced to ammonia by the bacteria. The host plant is most often of the family Leguminosa. Previously, Rhizobium species were informally classified in two groups, either as "fast-growing" or "slow-growing" to reflect the relative growth rates in culture. The group of "slow-growing" rhizobia has recently been reclassified as a new genus, Bradyrhizobium (Jordan, D. C. (1982) International Journal of Systematic Bacteriology 32:136). The fast-growing rhizobia include *Rhizobium trifolii, R. melliloti, R. leguminosarum* and *R. phaseolus*. These strains generally display a narrow host range. Fast-growing *R. japonicum* which nodulate *Glycine max* cv. Peking and fast-growing members of the cowpea Rhizobium display broader host range. The slow-growing rhizobia, a distinct genus now called Bradyrhizobium, include the commercially important soybean nodulating strains *Bradyrhizobium japonicum* (i.e.; USDA 110 and USDA 123), the symbiotically promiscuous rhizobia of the "cowpea group", and Bradyrhizobium sp. (Parasponia) (formerly *Parasponia Rhizobium*) which nodulates the non-legume Parasponia, as well as a number of tropical legumes including cowpea and siratro.

Nodulation and development of effective symbiosis is a complex process requiring both bacterial and plant genes. Several recent reviews of the genetics of the Rhizobium-legume interaction are found in Broughton, W. J., ed. (1982) *Nitrogen Fixation,* Volumes 2 and 3 (Clarendon Press, Oxford); Puhler, A. ed. (1983) *Molecular Genetics of the Bacteria-Plant Interaction* (Springer-Verlag, Berlin); Szalay, A. A. and Leglocki, R. P., eds. (1985) *Advances in Molecular Genetics of the Bacteria-Plant Interaction* (Cornel 1 University Publishers, Ithaca, N.Y.); Long, S. R. (1984) in *Plant Microbe Interactions* Volume 1, Kosuge, T. and Nester, E. W. eds. (McMillan, N.Y.) pp. 265–306; and Verma, D. P. S. and Long, S. R. (1983) International Review of Cytology (Suppl. 14), Jeon, K. W. (ed.), Academic Press, p. 211–245.

In the fast-growing species, the genes required for nodulation and nitrogen fixation are located on large Sym (symbiotic) plasmids. Although the process of recognition, infection and nodule development is complex, it appears that at least for the fast-growing rhizobia relatively few bacterial genes are directly involved and these are closely linked on the Sym plasmid. For example, a 14 kb fragment of the *Rhizobium trifolii* Sym plasmid is sufficient to confer clover-specific nodulation upon a Rhizobium strain cured of its Sym plasmid, as well as on an Agrobacterium strain which does not normally nodulate plants (Schofield et al., (1984) Plant Mol. Biol. 3:3–11). Nodulation and nitrogenase genes are localized on symbiotic plasmids in *R. leguminosarum* (Downie et al. (1983) Mol. Gen. Genet. 190:359–365) and in *R. meliloti* (Kondorosi et al. (1984) Mol. Gen. Genet. 193:445–452). In contrast, no Sym plasmids have been associated with the slow-growing rhizobia, *B. japonicum* or Bradyrhizobium sp. (Parasponia). The nitrogenase and nodulation genes of these organisms are believed to be encoded on the chromosome.

Fine structure genetic mapping has been used to locate individual nodulation genes in fast-growing rhizobia. Transposon mutagenesis, most often using the transposon Tn5, has identified about 10 nodulation genes associated with non-nodulation, delayed nodulation and altered host range phenotypes (Djordjevic et al. (1985) Mol. Gen. Genet. 200:263–271; Downie et al. (1985) Mol. Gen. Genet. 198:255–262; Kondorosi et al., 1984, and Innes et al. (1985) Mol. Gen. Genet. 201:426–432). Common nodulation genes designated nodABC and D, which are functionally and structurally conserved among the fast-growing rhizobia, have been identified by hybridization studies and cross-species complementation experiments (Banjalvi et al. (1981) Mol. Gen. Genet. 184:318–325; Djordjevic et al. (1985) Plant Mol. Biol. 4:147–160; Kondorosi et al. (1984) Mol. Gen. Genet. 193:445–452; and Fisher et al. (1985) Applied Environ. Microbiol. 49:1432–1435). Both Bradyrhizobium sp. (Parasponia) (Marvel et al. (1985) Proc. Natl. Acad. Sci. USA 82:5841–5845) and *B. japonicum* (Russel et al. (1985) J. Bacteriol. 164:1301–1308) contain nodulation genes which can functionally complement mutations in fast-growing rhizobia and which show strong structural homology to nodulation gene regions of *R. meliloti* and *R. leguminosarum*. In addition to the common nod genes, adjacent regions (IV and V) which are involved in host specificity of nodulation (nodG and nodH) have been identified in *R. meliloti* (Kondorosi et al. 1984) and *R. trifolii* (Djordjevic et al. 1985; Rolfe et al. (1985) *Nitrogen Fixation Research Progress,* Evans et al. (eds.), Martinus Nijhoff, pp. 79–85.

DNA sequencing of the common nod gene region has revealed similarities in organization of these nod genes in fast growing rhizobia, as shown in FIG. 1. The open reading frames of nodA, B and C are grouped sequentially and believed to be coordinately transcribed as a single transcriptional unit. The nodD open reading frame reads divergently from the nodABC operon (Egelhoff et al. (1985) DNA 4:241–248; Jacobs et al. (1985) J. Bacteriol. 162:469–476; Rossen et al. (1984) Nucleic Acids Res. 12:9497–9508; and Torok et al. (1984) Nucl. Acids Res. 12:9509–9524; Schofield (1985) *Nitrogen Fixation Research Progress,* Evans et al. (eds.) Martinus Nijhoff, p. 125; and Rolfe et al., ibid., 1985). The DNA sequence between nodA and nodD is presumed to contain divergent promoters for each of these regions.

Sym plasmid encoded nodulation genes of Rhizobium strains and their analogues in Bradyrhizobium strains affect the early stages of nodule formation including host-bacterium recognition, infection and nodule development. Among strains that infect a particular host, there is some variation in the rates of initiation of nodulation which is reflected ultimately in differences in competitiveness between strains for nodule occupancy on the host. Strains which initiate infection and nodules earlier will occupy a greater portion of the nodules on a given plant. The timing of the initiation of nodulation by a strain appears to be genetically determined. Improving the competitiveness of a specific Rhizobium is an important part of the development of improved inocula for legumes. A more effective Rhizobium strain, which would likely constitute an improved inoculum, must be able to out-compete the indigenous rhizobia population for nodule occupancy in order for their improved qualities to impact on the inoculated legume.

The precise biochemical role of the nod genes and their products in nodule development is unknown. Attempts to isolate nod gene mRNA and protein products from free-living Rhizobium have been unsuccessful (Kondorosi et al. 1984). Protein products of several nod genes have, however, been obtained by fusion of nod genes to strong *E. coli* promoters (Schmidt et al. (1984) EMBO J. 3:1705–1711; and John, M. et al. (1985) EMBO J. 4:2425–2430) or in an *E. coli* in vitro transcription/translation system (Downie et. al. (1985) Mol. Gen. Genet. 198:255–262).

The establishment of nitrogen-fixing nodules is a multi-stage process involving coordinated morphological changes in both bacterium and plant, so it is expected that the rhizobial nodulation genes are under precise regulatory control. It has been suggested that an exchange of signals between plant and bacterium is requisite for mutual recognition and coordination of the steps of infection and nodulation development (Nutman, P. S. (1965) in *Ecology of Soil Borne Pathogens*, eds. F. K. Baker and W. C. Snyder, University of California Press, Berkeley, pp. 231–247; Bauer, W. D. (1981) Ann. Rev. Plant Phys. 22:407–449; and Schmidt, E. E. (1979) Ann. Rev. Microbiol. 33:355–376). For example, legume exudates have been linked to control of nodulation. Exudates have been reported to both stimulate (Thornton (1929) Proc. Royal Soc. B 164:481; Valera and Alexander (1965) J. Bacteriol. 89:113–139; Peters and Alexander (1966) Soil Science 102:380–387) or inhibit (Turner (1955) Annals Botany 19:149–160; and Nutman (1953) Annals Botany 17:95–126) nodulation by rhizobia.

Recently, Baghwat and Thomas (1982) Applied Environ. Microbiol. 43:800–805 described a stimulatory factor from legume exudates that was thermostable, was high molecular weight (about $2\times10^5$) and was composed of protein and neutral hexoses. This factor was associated with elimination of nodulation delay in a certain cowpea Rhizobium strain. Halverson and Stacey (1984) Plant Physiol. 74:84–89; and (1985) Plant Physiol. 77:621–624 reported an exudate factor having a similar affect on nodulation initiation in *B. japonicum* USDA 110 mutants. In contrast to Baghwat and Thomas (1982), this stimulator of nodulation is described as a heat and trypsin sensitive protein; a galactose, specific lectin. Diverse chemicals have been identified as stimulators or inhibitors of nodulation. Reported stimulators of nodulation include inositol, indole, 2-phenol-n-butyric acid, D-leucine, barbituric acid, pyridine-3-sulfonate and quercetin (Molina and Alexander (1967) Can. J. Microbiol. 13:819–827; and Weir (1960) Phyton 15:109–118).

The chemical factors in legume exudates that are responsible for stimulation of nod gene expression have been identified. U.S. Patent Application Serial No. 844,870 filed Mar. 27, 1986, identified a structural related class of molecules, certain substituted flavones and flavanones as nod gene inducing factors. Individual purified molecules, either isolated from clover exudates or available from commercial sources, were found to induce expression of certain nod genes.

SUMMARY OF THE INVENTION

The present work discloses the location and sequence of three nodulation gene promoters which activate gene expression in response to chemical factors in legume exudate. Two of these promoters control expression of the nodABC(IJ) operon and the nodFE operon, respectively, of *R. trifolii;* the third promoter controls expression of the nodulation gene operon nodKABC of Bradyrhizobium sp. (Parasponia). The regulation of nod gene expression has been examined using nod gene fusions constructed by insertion of a transposon MudI1734 into nodulation genes. This transposon contains a promoterless lacZ (β-galactosidase) gene from *E. coli*, so expression of the nod-lac fusion reflects expression of the nod gene into which it is inserted and also reflects the regulatory control of the nod gene promoter. *R. trifolii* genes nodABCEFGHI and J are all demonstrated to be inducible by legume exudates. In contrast, nodD is found to be constitutively expressed in free-living *R. trifolii*. Expression of nodD is not stimulated by legume exudate. *R. trifolii* nod genes, except nodD, are induced by legume exudates from a number of legumes including clover; pea, bean, soybean, alfalfa and siratro, and not by exudates of non-leguminous plants.

It is an important feature of this work that the promoter regions of the nodABC(IJ) and nodFE genes of *R. trifolii* are found to contain a reiterated highly conserved sequence about 76 base pairs (bp) long. The reiteration of the sequence in the nodABC(IJ) and nodFE promoter regions are 78% homologous. A shorter 27 bp core element within the 76 bp sequence is 93% homologous between the two iterations with 25 of 27 bp of the core sequence conserved. An analogous sequence, previously reported but unidentified, is found in the *R. meliloti* nodA promoter region (Torok et al., 1983, and Egelhoff et al., 1985). Shearman et al. 1986 demonstrate the presence of the consensus regulatory sequence in *R. leguminosarum* nod gene promoter regions. The *R. meliloti* promoter region contains a 27 bp sequence identical to the *R. trifolii* nodABC 27 bp core sequence. Surprisingly, the nodKABC promoter region of slow-growing Bradyrhizobium sp. (Parasponia) also contains a sequence analogous to those identified in *R. trifolii* and *R. meliloti* which is 70% homologous to the nodABC 27 bp core sequence. The *R. leguminosarum* nodA and nodF promoter regions also contain analogous regulatory sequences (Shearman et al. 1986). The iterated sequences are regulatory sequences which function in the induction of nodulation genes in response to chemical factors (nodulation inducing factors) in legume exudate. A comparison of four reiterations of the conserved sequence identifies a consensus sequence (FIG. 4) whose presence in the promoter region of a gene is required for the induction of that gene by nodulation inducing factors in plant exudate. Recently, iterations of the consensus sequences have been identified in *B. japonicum* USDA 123 and USDA 110 adjacent to the nodD coding region (U.S. patent application Ser. No. 875,297 filed Jun. 17, 1986, now abandoned).

The regulatory sequences and the nodulation gene promoter-containing DNA fragments of the present invention are useful as hybridization probes for the identification of legume exudate-inducible promoters. As an example of this utility, a third iteration of the conserved promoter sequence has been identified in *R. trifolii* nod region V by hybridization experiments using a DNA probe containing the *R. trifolii* nodABC conserved regulatory sequence.

It is a principal object of this invention to identify a regulatory DNA promoter sequence which functions in the induction of gene expression by chemical factors in legume exudates. These chemical factors which are nodulation inducing factors have recently been identified as substituted flavones and flavanones (U.S. application Ser. No. 844,870, filed Mar. 27, 1986). The sequences and the isolated promoter containing DNA fragments provided are useful in the construction of legume exudate-inducible chimeric genes containing legume exudate-inducible promoters and heterologous structural genes placed under the control of the promoter. Such genetic constructions are useful for selective controlled expression of a variety of structural genes.

It is another object of this invention to provide recombinant DNA molecules containing legume exudate-inducible chimeric genes. These constructions are made using the sequences and DNA fragments of the present invention either directly or as probes to identify DNA fragments having similar regulatory function. Alternatively, the sequence information provided herein can be used to prepare synthetic regulatory sequences which function in the induction of genes by chemical nodulation inducing factors.

It is another object of this invention to provide a method of selectively expressing a structural gene employing the DNA sequences and fragments of the present invention.

BRIEF DESCRIPTION OF THE FIGURES

Figure 2A:
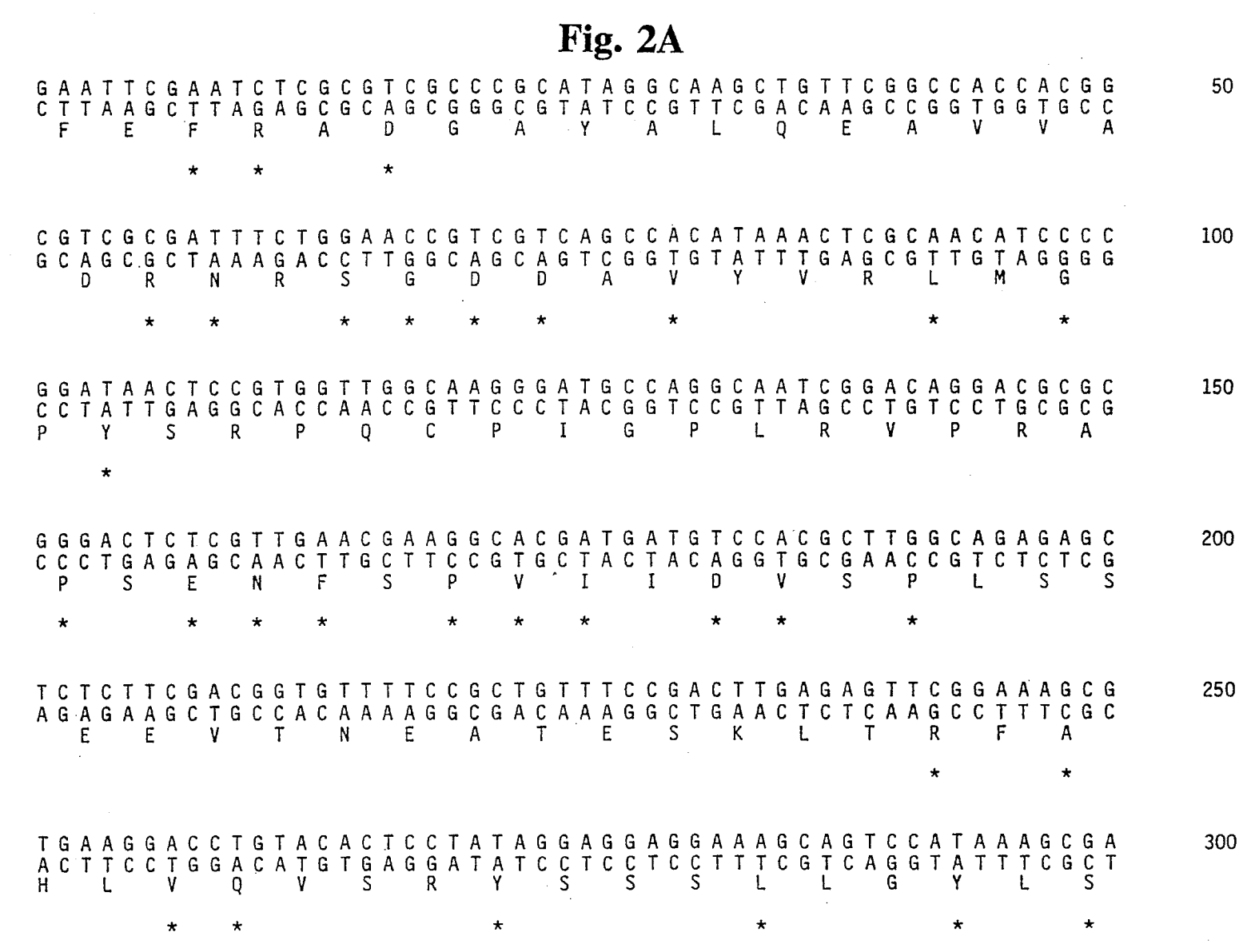
Figure 2B:
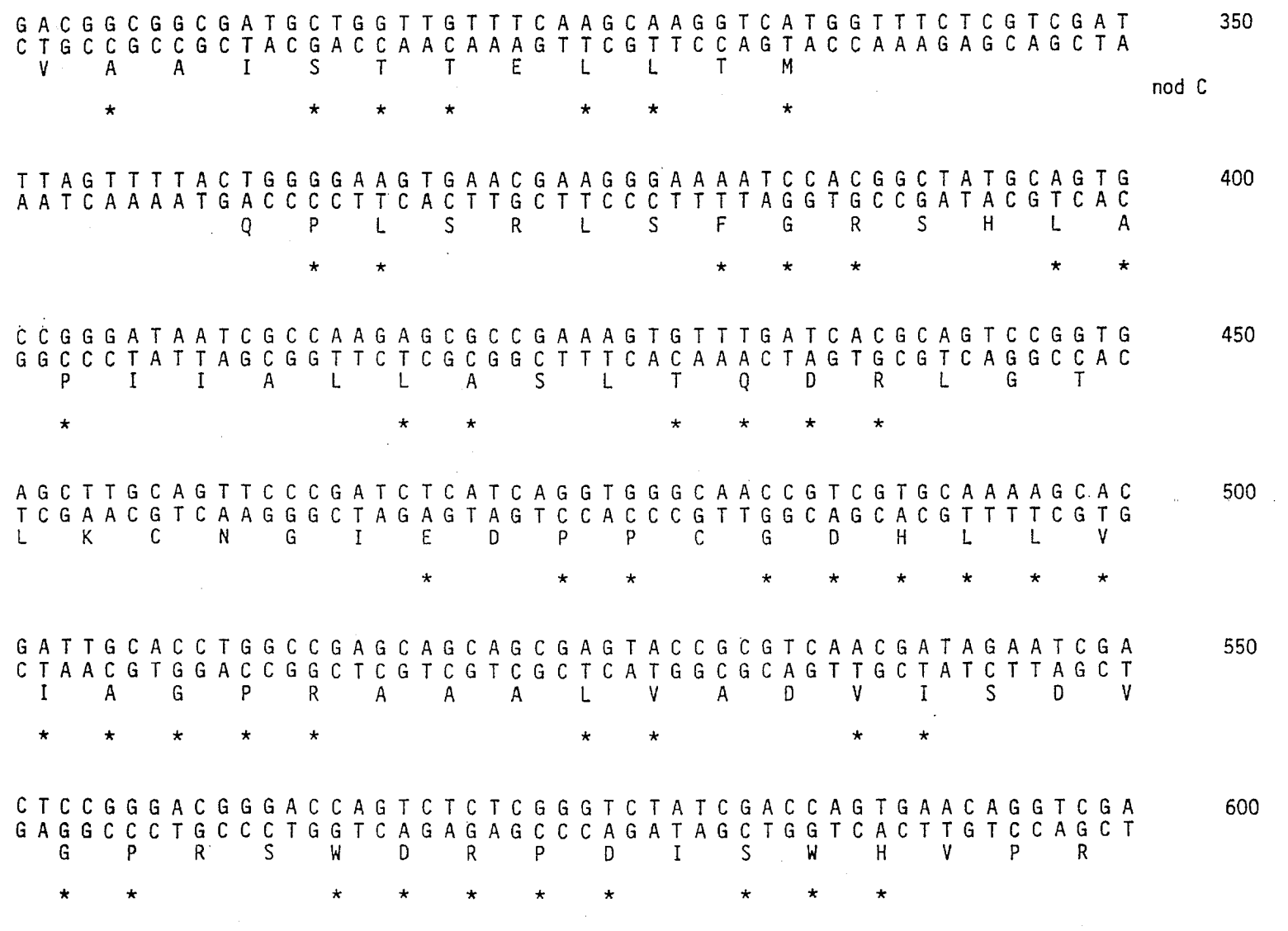
Figure 2C:
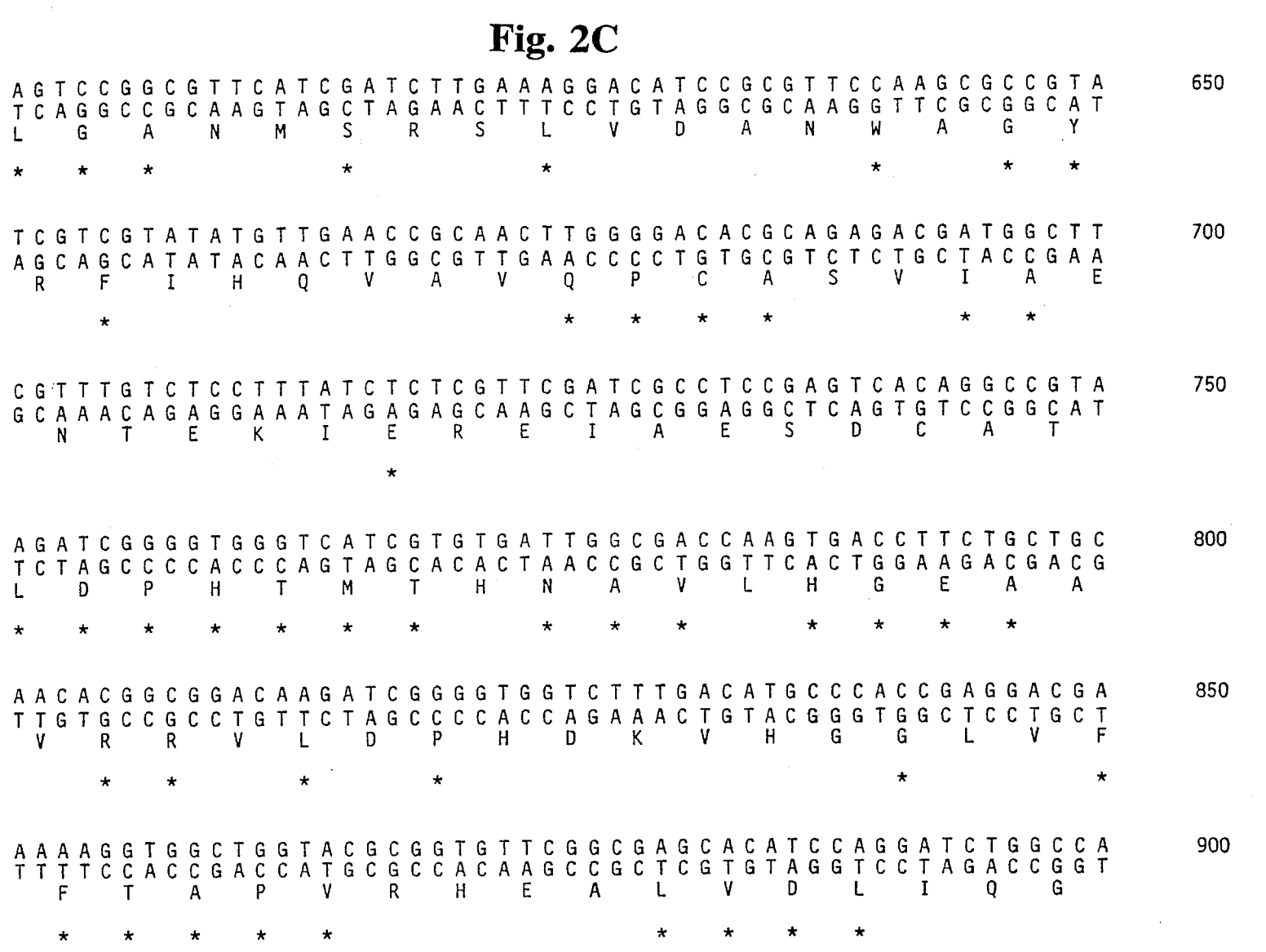
Figure 2D:
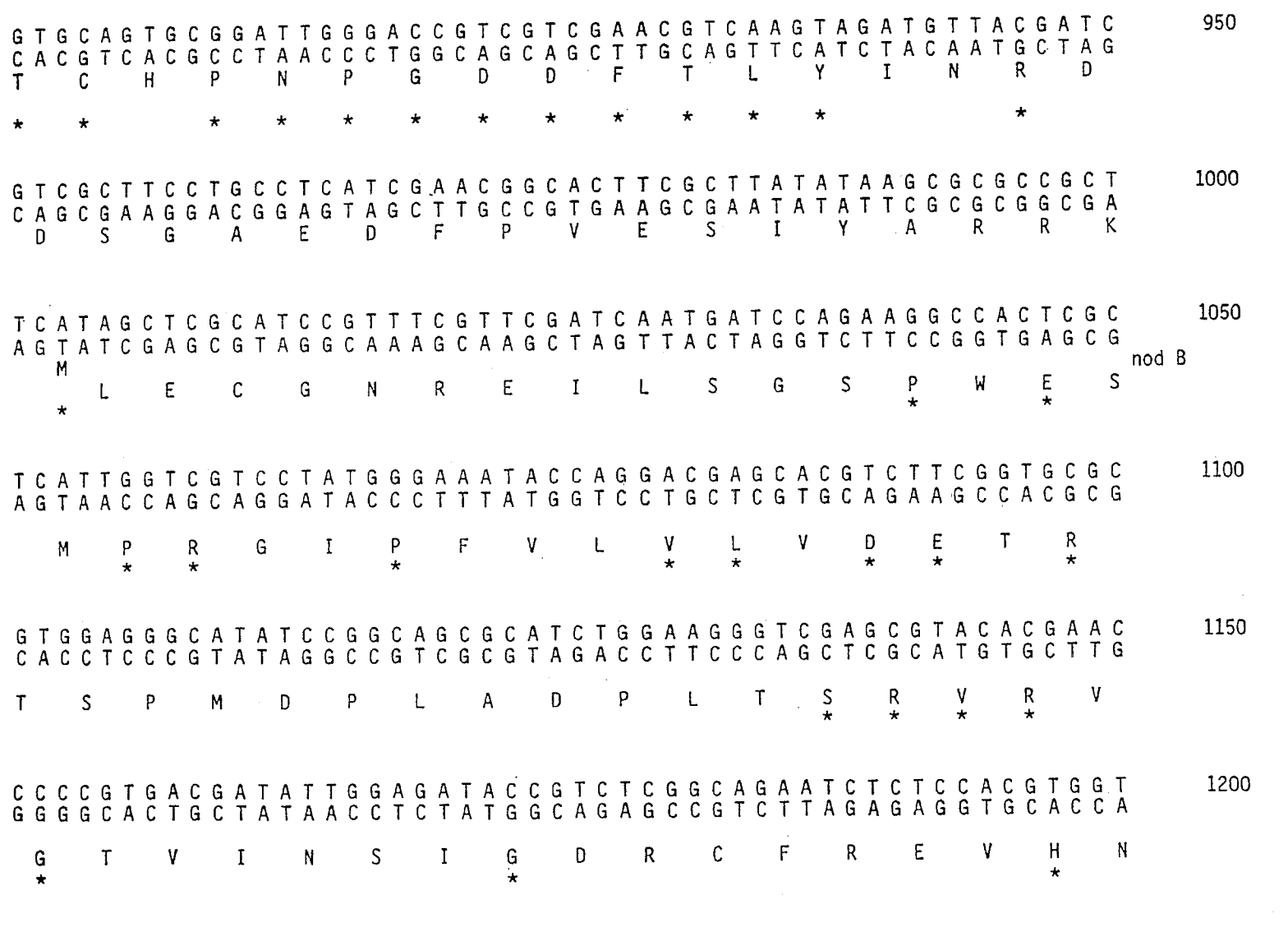
Figure 2E:
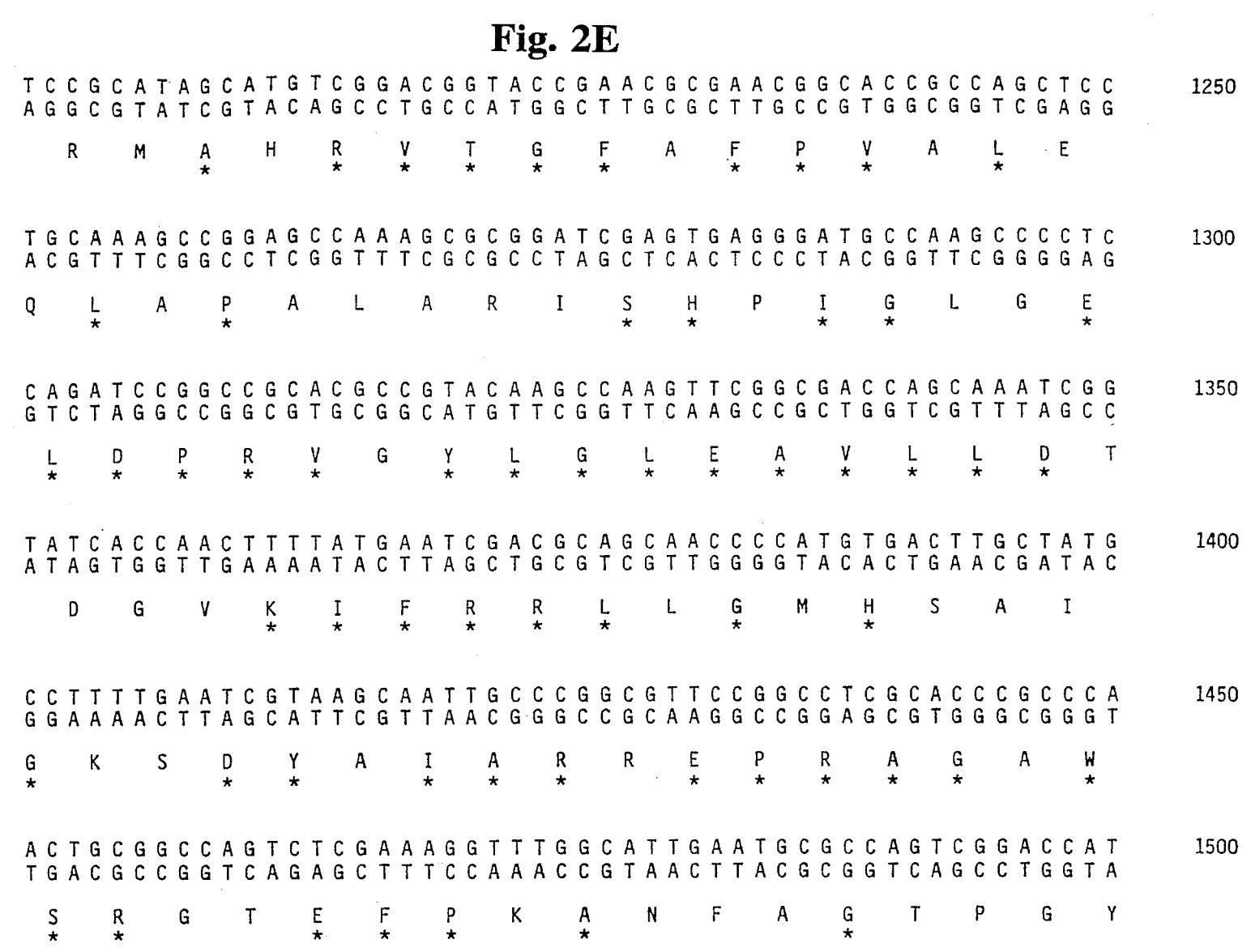
Figure 2F:
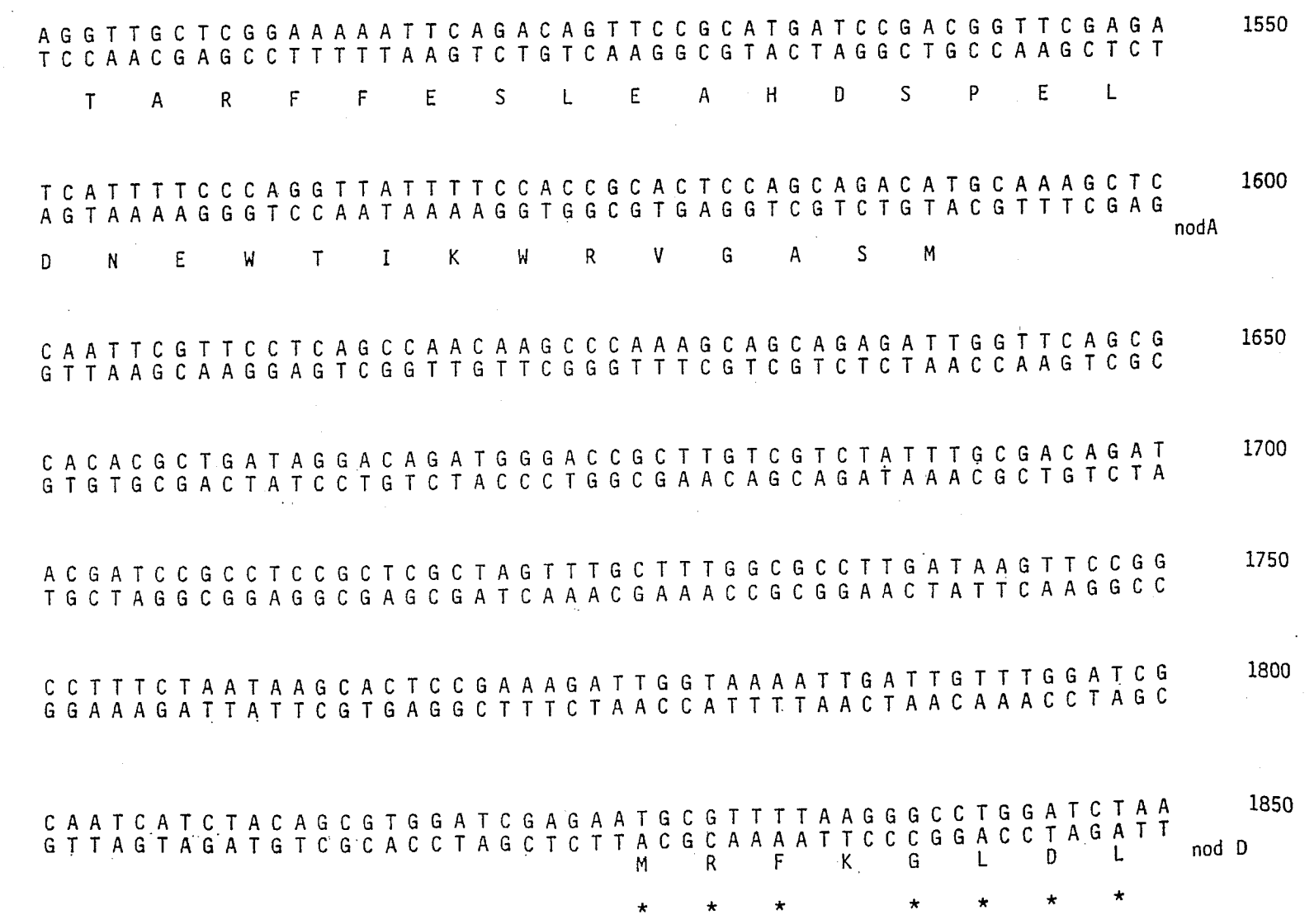
Figure 2G:
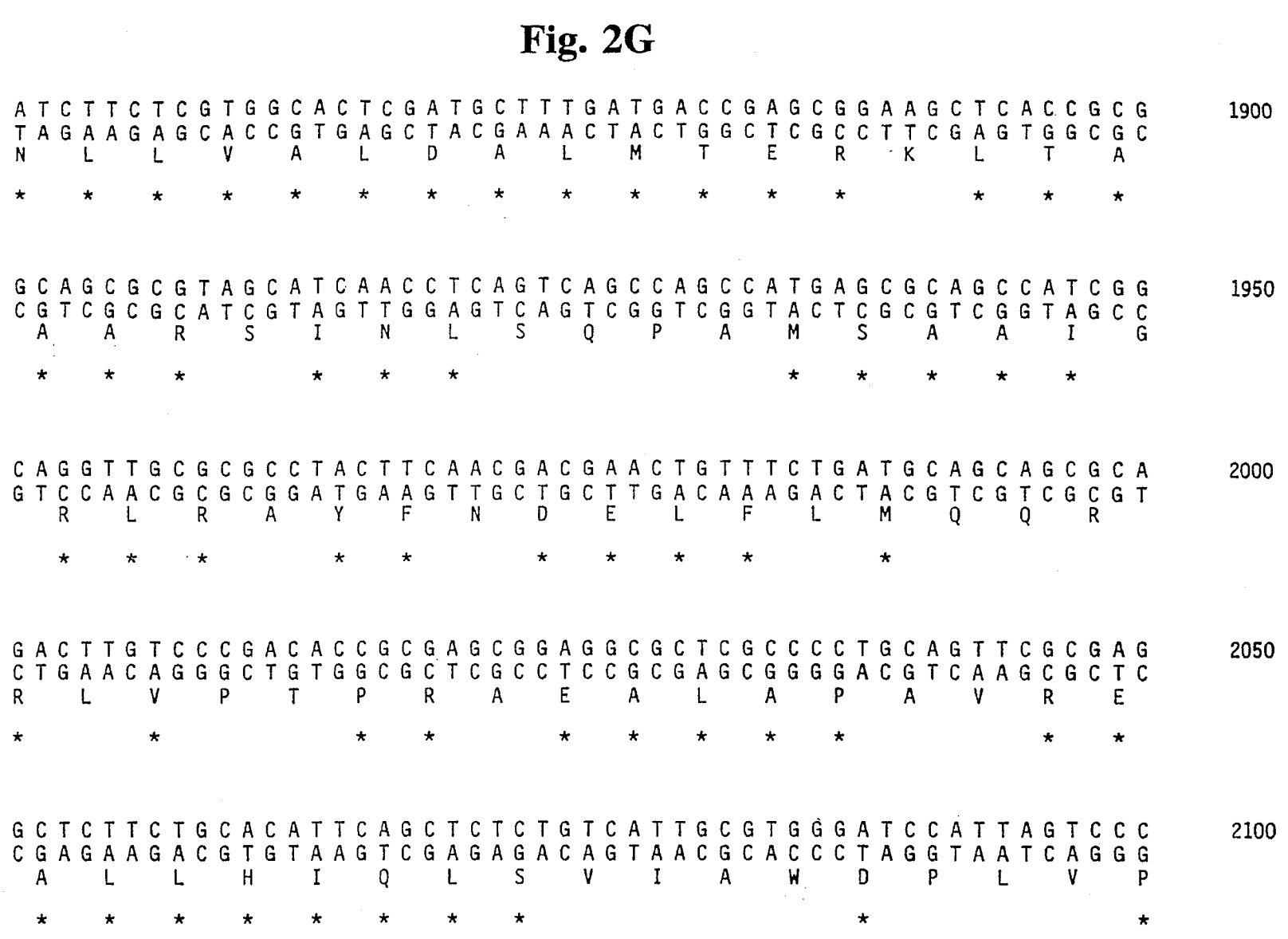
Figure 2H:
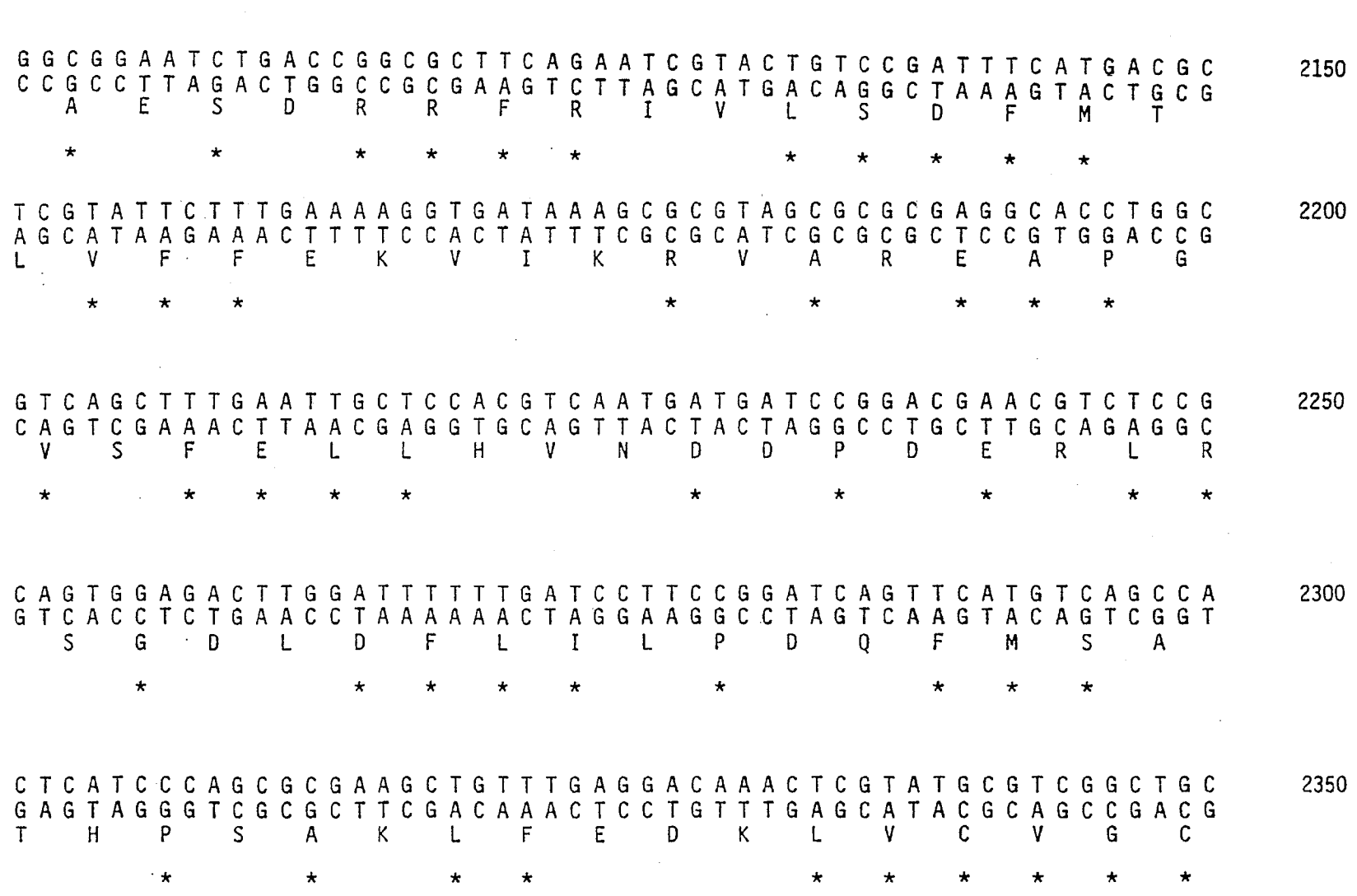
Figure 2I:
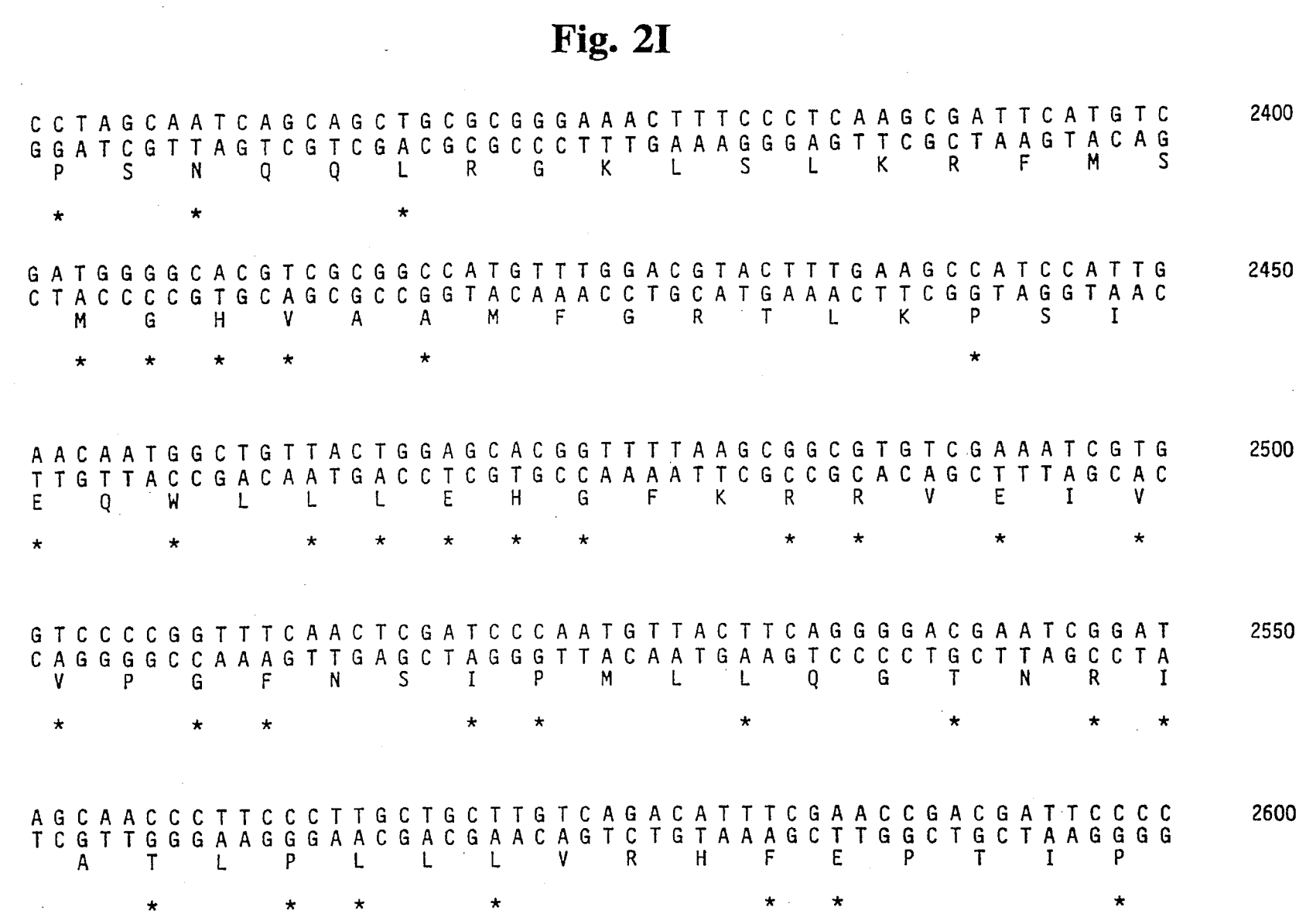
Figure 2J:
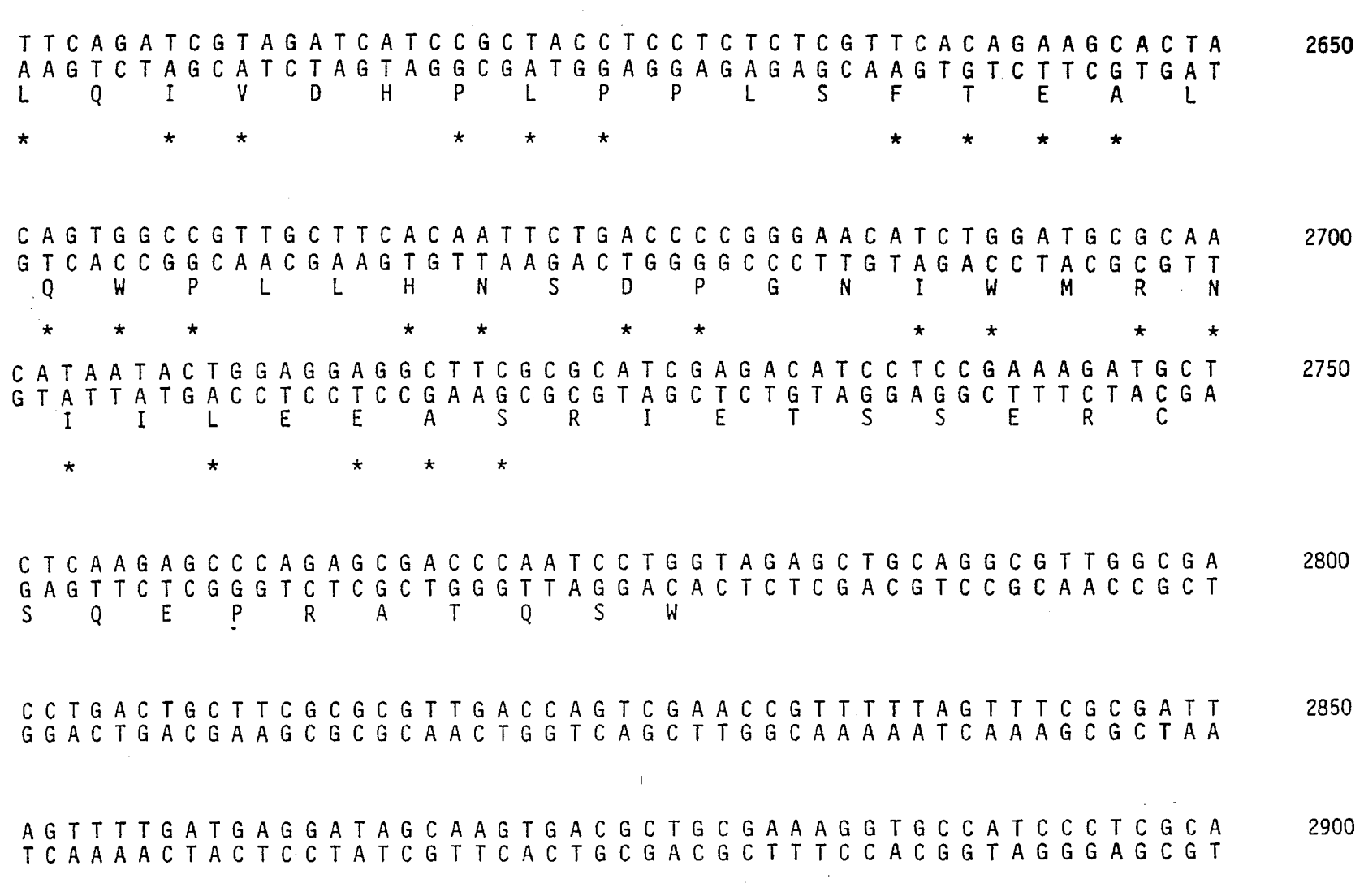
Figure 2K:
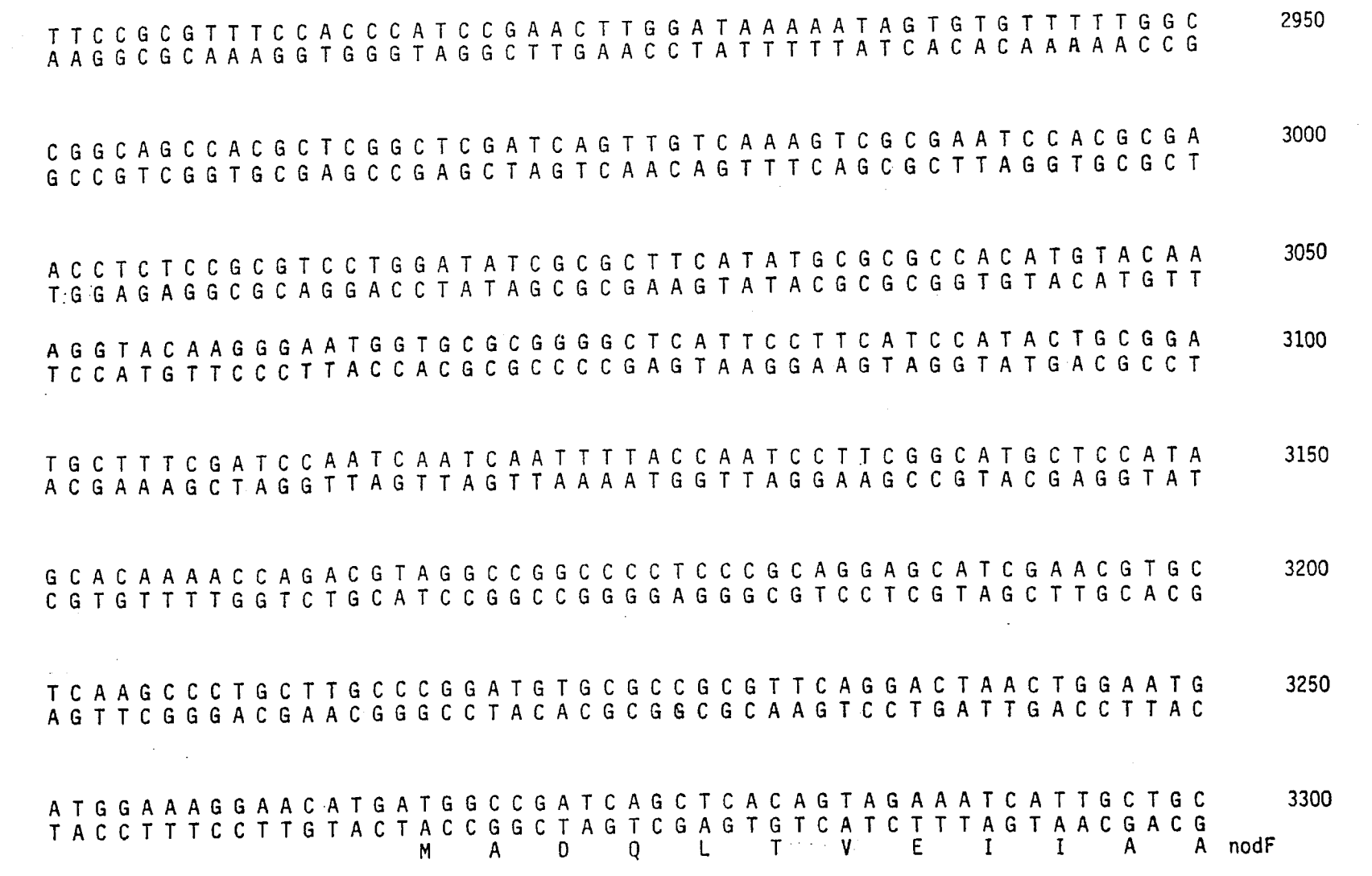
Figure 2L:
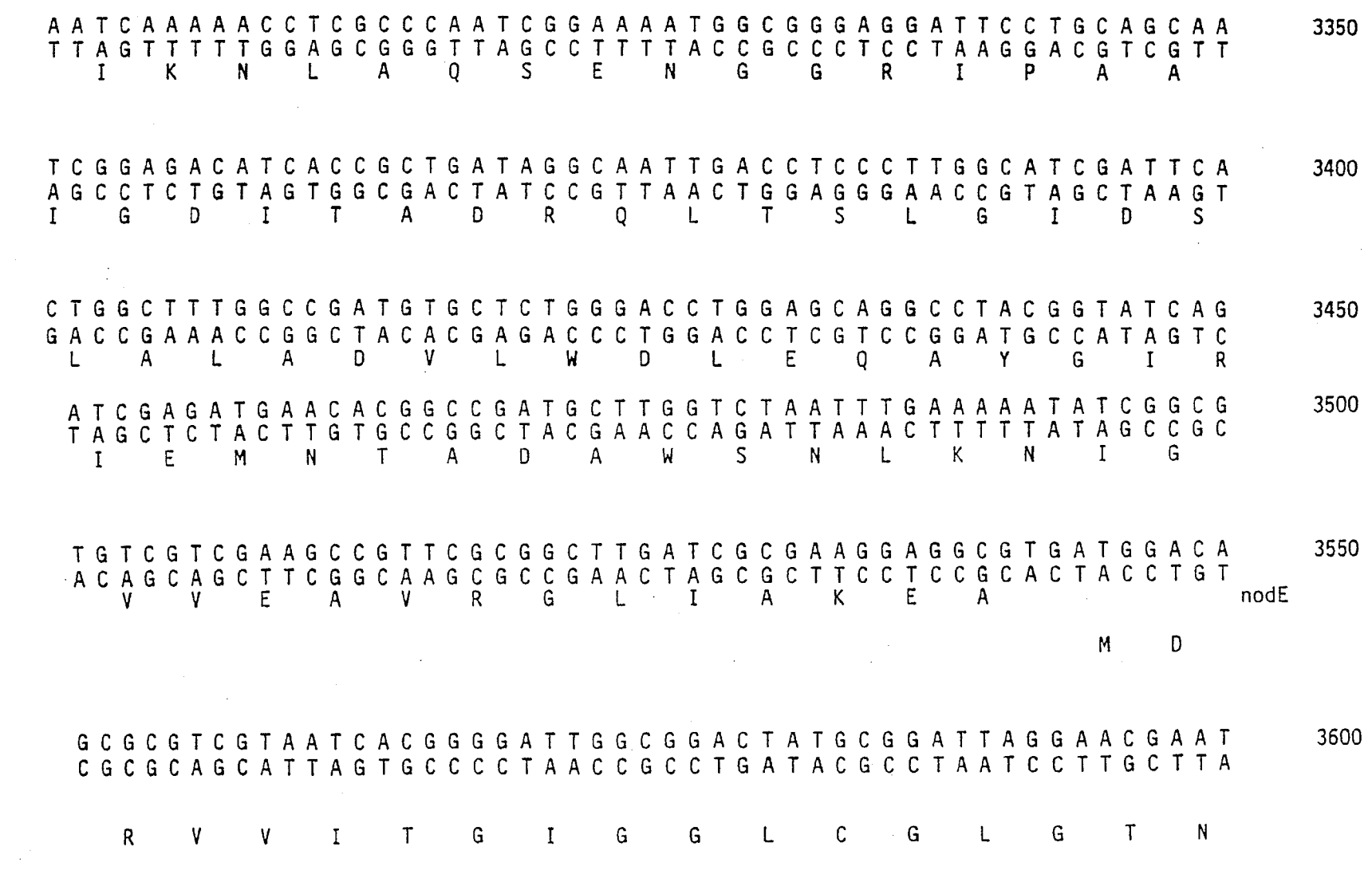

FIG. 2 is the nucleotide sequence of the 3668-bp EcoRI-BglII nod gene fragment of *R. trifolii* strain ANU843. The predicted amino acid sequences of the gene products are indicated. Table 4 provides the amino acid abbreviations used in FIG. 2. Asterisks indicate the invariant amino acids in the homologous gene products of *R. trifolii, R. leguminosarum, R. meliloti* and Bradyrhizobium sp. (Panasponia). The promoter region conserved sequence, between the nodD gene and nodA gene, and the nodD and nodF gene are underlined. This sequence has recently been published (Scott (1986) Nucleic Acids Res. 14:2905–2919 ).

FIG. 3 is the nucleotide sequence of the untranslated region (promoter region) between nodD and the nodKABC gene cluster in Bradyrhizobium sp. (Parasponia) ANU 289. The conserved regulatory sequence is enclosed in brackets and regions of greatest conservation with other iterations are underlined.

FIG. 4 is a comparison of the conserved legume regulatory sequence of nod genes from *R. trifolii, R. meliloti* and Bradyrhizobium sp. (Parasponia). The sequences are aligned for best fit, with regions of greatest conservation underlined. The consensus sequence of the four iterations is shown on the bottom line. Conventional nomenclature for incompletely specified bases is used as described in J. Biol. Chem (1986) 261:13–17.

DETAILED DESCRIPTION OF THE INVENTION

Figure 1:
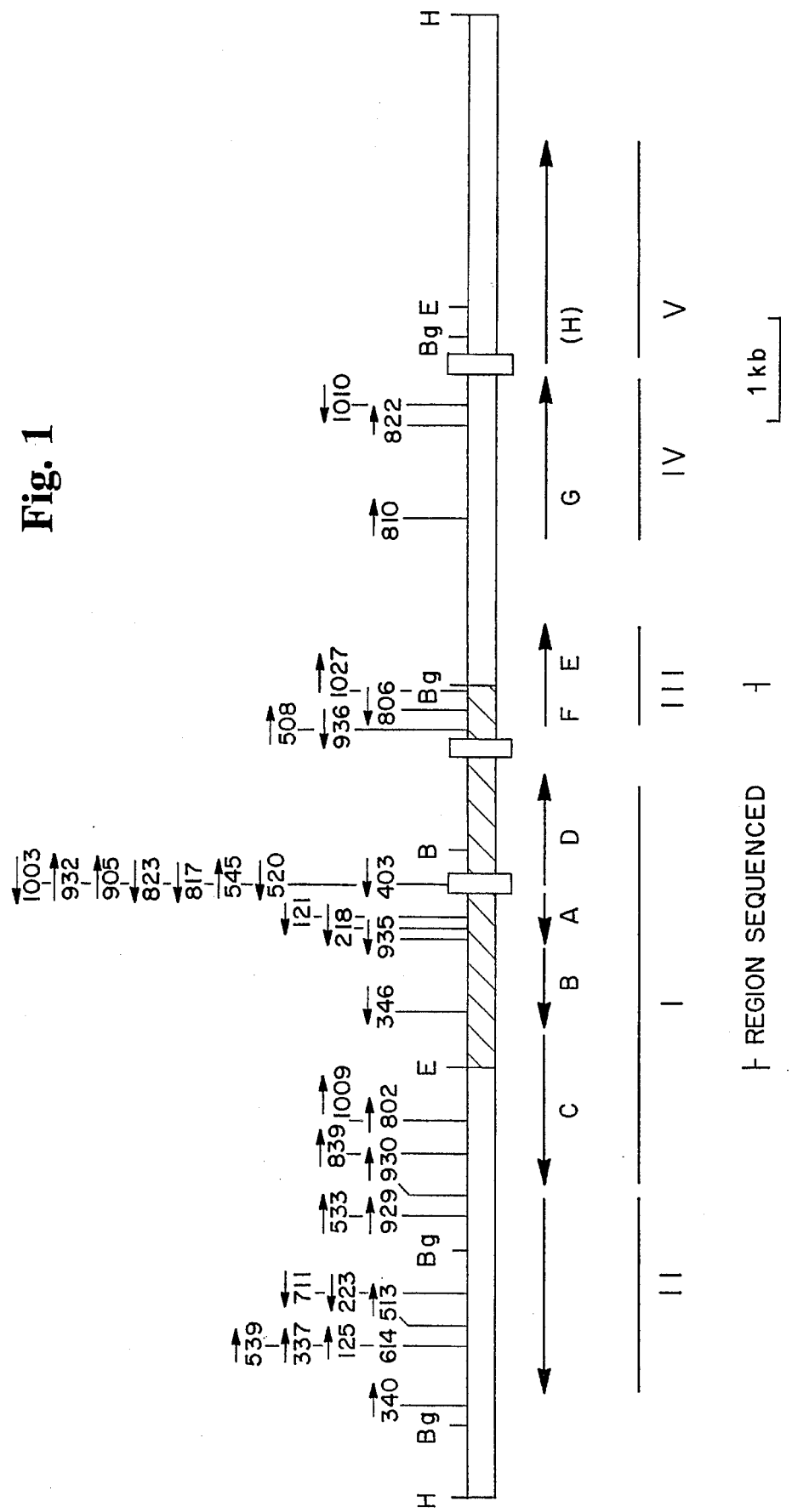
FIG. 1 is a DNA restriction map showing the location of MudI1734 (kan, lac) insertions in the 14 kb HindIII fragment of the *R. trifolii* nod region from the Sym plasmid of ANU843. Insertions are indicated by vertical lines with numbers. Orientation of the β-galactosidase gene is shown for each insertion by an arrow above the number. The areas defined by regions I, II, III, IV and V are indicated and represent phenotypically distinct genetic regions. The positions of nodA, nodB, nodC, nodD, nodE and nodF were determined from sequencing data presented infra and correlated with the phenotypes of transposon induced mutants of these regions (Djordjevic et al. 1985; Innes et al., 1985). Region II is believed to contain at least two other open reading frames designated nodI and nodJ. Region IV and Region V are presently believed to each contain one open reading frame, designated nodG and nodH, respectively. The direction of transcription within genes or regions is signified by heavy arrows. The portion of the *R. trifolii* nod region that was sequenced (FIG. 2) is indicated by hatching. The locations of three iterations of the conserved cross regulatory sequence are indicated by boxes.

The term promoter is used in the art to designate the nucleotide sequence adjacent to the 5' end of a structural gene which is involved in the initiation of transcription.

Promoters contain DNA sequence elements which insure proper binding and activation of RNA polymerase, influence where transcription will start, and affect the level of transcription. Further, specific regulatory sequences within or adjacent to promoters that are functional in the regulation (induction and repression) of gene expression responsive to stimuli or specific chemical species may also be present (Raibaud and Schwartz (1984) Ann. Rev. Genet. 18:173–206). The sizes of promoters are variable. In many cases, promoter activity is confined to approximately 200 bp of sequence in the 5' direction (or downstream) to the site of transcript initiation. However, sequences out to approximately 400 bp 5' to the structural gene have been implicated in the regulation of gene expression of certain genes. The majority of promoters control initiation of transcription in one direction only so in order to be under the control of a promoter, a structural gene must usually be located downstream (in the 3' direction) of the promoter and in the correct orientation with respect to the promoter. The distance between the promoter and the structural gene is believed to be an important factor in gene expression level. One or several genes may be under the control of a single promoter or, conversely, one or more promoters may control a single structural gene.

Comparisons of promoter sequences of a number of *E. coli* genes have revealed conserved sequence elements at –10 bp (10 nucleotides 5' to the site of initiation of transcription) and –35 bp (Rosenberg and Court (1979) Ann. Rev. Genet. 13:319–353). These sequences have been implicated in RNA polymerase binding. An average *E. coli* promoter can be represented by a consensus sequence "5'-TTGACA-TATAAT-3'". The distance between the two elements in this consensus sequence is also generally conserved at between 15–19 bp. Promoters having similar sequence elements have been found in other gram-negative bacteria. In contrast, eukaryotic promoters have sequence elements that are distinct from the consensus prokaryotic promoters of *E. coli*. Eukaryotic promoters are not usually functional in prokaryotes, and prokaryotic promoters are not usually functional in eukaryotes.

Comparison of the DNA sequence of promoters of genes that are regulated by similar mechanisms has revealed distinct promoter sequences associated with regulation. For example, comparison of the promoters of the nitrogenase genes (nif) in *Klebsiella pneumoniae* and the fast- and slow-growing rhizobia reveals a nif promoter consensus sequence distinct from the *E. coli* consensus sequence 5'. . . YTGGCAYG TTGCW . . . 3' where Y is C or T and W is A or T and in which the two sequence elements are separated by about 5 bases (Ausubel (1984) Cell 37:5–6; Better et al. (1983) Cell 85:479–485).

Environmental factors such as temperature, light and oxygen tension, and chemical species such as nutrients, metabolites, heavy metal ions and steroids have been found to regulate gene expression. Factors that induce expression as well as factors that repress expression of genes have been identified. The exact mechanisms of regulation by such signals or stimuli is likely to be complex involving multiple chemical interactions. By analogy to previous mechanistic studies of regulation, however, regulatory control is expected to involve changing the ability of RNA polymerase to bind to DNA sequences in the promoter region. One possible mechanism is the binding of regulatory protein to a DNA sequence at or near the position of binding of RNA polymerase to enhance or prevent transcription. A second possible mechanism is direct or indirect interaction of a signal (inducer or repressor) molecule with RNA polymerase, itself, to change its specificity for recognition and binding to a DNA sequence of the promoter. In either case, specific sequence(s) within the promoter would be involved in the mechanism of regulation. Depending upon the mechanism of regulation, the presence within a promoter region of one or several sequences can be important to the regulation of promoter activity.

The nodulation gene promoters and regulatory sequences of the present invention function in the induction of nod genes by nodulation inducing factors and compositions. The promoters of the nodABC, nodFE and region II, IV and V in *R. trifolii* and nodKABC in Bradyrhizobium sp. (Parasponia) are examples of legume exudate-inducible promoters (see Table 3).

The term recombinant DNA molecule is used herein to distinguish DNA molecules in which heterologous DNA sequences have been artificially cleaved from their natural source or ligated together by the techniques of genetic engineering, for example by in vitro use of restriction enzymes or ligation using DNA ligase.

The process of cloning a DNA fragment involves excision and isolation of the DNA fragment from its natural source, insertion of the DNA fragment into a recombinant vector and incorporation of the vector into a microorganism or cell where the vector and inserted DNA fragment are replicated during proliferation of the microorganism or cell. The term cloned DNA fragment or molecule is used to designate a DNA fragment or molecule produced by the process of cloning and copies (or clones) of the DNA fragment or molecule replicated therefrom.

Expression of a gene requires both transcription of DNA into mRNA and the subsequent translation of the mRNA into protein products. Because gene regulation usually occurs at the level of transcription, transcriptional regulation and promoter activity are often assayed by quantitation of gene products (mRNA or proteins) or by assaying for enzymatic activities of gene products. For example, promoter regulation and activity has often been quantitatively studied by the fusion of the easily assayable *E. coli* lacZ gene to heterologous promoters (Casadaban and Cohen (1980) J. Mol. Biol. 138:179–207; Okker et al., 1984; Leong et al., (1985) Nucleic Acids Res. 13:5965; Khoos and Kaiser (1984) Proc. Natl. Acad. Sci. USA 81:5816–5820; and Leglocki et al. (1984) Proc. Natl. Acad. Sci. USA 81:5806–5810). The structural gene for chloramphenicol acetyl transferase (CAT) is another gene commonly used to detect activity of a promoter. Such structural genes are termed "reporter" genes, which when combined with a given promoter (usually heterologous) provide a ready assay for promoter activity.

A consensus sequence is an average nucleotide sequence obtained by comparison of a set of DNA sequences which have a similar function. Consensus sequences have been used to describe the conserved regions within promoters and other functional sequences such as splice sites.

The term homology is used in the art to describe a degree of nucleotide sequence identity between polynucleotides (RNA or DNA). Sequences that are homologous across species boundaries or between functionally similar elements are also said to be conserved. The presence of sequence homology or conservation is often used to support a genetic or functional relationship between nucleotide sequences. The degree of homology between polynucleotides is quantitatively determined as a percent homology if the sequences are known. In the absence of sequence information for comparison, the presence of homology is preferably determined operationally by hybridization experiments. A single strand of DNA or RNA will bind or hybridize to other single stranded polynucleotides whose sequences are complementary or partially complementary to their own. The strength of this binding depends on a number of factors including the degree of homology between the sequences, the nucleotide composition of the sequences, the length of the sequences and the experimental conditions used for hybridization. When hybridization is done under stringent conditions, the temperature and washing conditions of the hybridization experiment are adjusted to minimize hybridization of mismatched sequences. In the absence of sequence information, the stringency of hybridization conditions can be adjusted by the use of appropriate positive and negative controls.

The promoters and regulatory sequences described herein function in the induction of gene expression in response to nodulation gene inducing compositions which contain nodulation gene inducing factors. Nodulation gene inducing compositions include, among others, exudates of leguminous plant roots and extracts of leguminous plant roots. Nodulation gene inducing factors are those chemical factors described in U.S. patent application Ser. No. 844,870, filed Mar. 27, 1986, which is hereby incorporated by reference. Nodulation gene inducing factors include, among others, the structurally related flavones: 7,4' dihydroxyflavone, apigenin, morin, and luteolin; and the flavanone: naringenin. Nodulation gene expression, as assayed herein by expression of lac fusions, is induced by placing legume roots in contact with either bacterial suspensions in liquid medium or with bacterial lawns grown on agar plates. These results are consistent with the excretion by legume roots of chemical factors which induce gene expression. Compositions having nod gene inducing activity can also be prepared by extraction of root or seed material. Root exudates from a variety of legumes have been found to contain inducing activity, while exudates from non-leguminous plants do not. Root exudates contain a rather complex mixture of components (Hale et al. (1978) in *Interactions Between Non-Pathogenic Soil Microorganisms and Plants* (Dommergues and Krupa, eds.) Elsevier, Amsterdam, The Netherlands, pp. 163–197), only one or several of which may be active as inducers.

Except as noted hereafter, standard techniques for cloning, DNA isolation, amplification and purification, for enzymatic reactions involving DNA ligase, DNA polymerase, restriction endonucleases and the like and various separation techniques are those known and commonly employed by those skilled in the art. A number of standard techniques are described in: Maniatis et al. (1982) Molecular Cloning, Cold Spring Harbor Laboratory, Cold Spring Harbor, N.Y.; Wu (ed.) (1979) Meth. Enzymol. 68; Wu et al. (eds.) (1983) Meth. Enzymol. 100 and 101; Grossman and Moldave (eds.) (1980) Meth. Enzymol. 65; Miller (ed.) (1972) Experiments in Molecular Genetics, Cold Spring Harbor Laboratory, Cold Spring Harbor, N.Y.; Old and Primrose (1981) Principles of Gene Manipulation, University of California Press, Berkeley; Schleif and Wensink (1982) *Practical Methods in Molecular Biology;* Glover (ed.) (1985) DNA Cloning Vol. 1 and II, IRL Press, Oxford, UK; Hames and Higgins (eds.) (1985) *Nucleic Acid Hybridization,* IRL Press, Oxford, UK; and Sellow and Hollaender (1979) *Genetic Engineering: Principles and Methods,* Vols. 1–4, Plenum Press, N.Y., which are incorporated by reference herein. Abbreviations, where employed, are those deemed standard in the field and commonly used in professional journals such as those cited herein.

R. trifolii Nodulation Genes

In *R. trifolii* ANU843 host specific nodulation genes are encoded within a 14 kb HindIII fragment of the symbiosis plasmid (Schofield et al. 1984). Extensive mutagenesis of this nodulation region using transposon Tn5 (Djordjevic et al. 1985) has led to the identification of three specific regions, designated I, II and III (see FIG. 2) which affect nodulation ability. Mutations in region I (approximately 3.5 kb long) affect root hair curling ability and abolish infection thread formation (both nod⁻). Mutations in regions II and III show exaggerated root hair curling (Hac⁺⁺) on clover. Some region II mutants confined to approximately 1.1 kb show greatly reduced nodulation ability. Mutants in region III (approximately 1.5 kb) show non-wild-type host range properties.

A number of lac operon transcription fusions to several of the nodulation genes in this region have been prepared in order to examine regulation of the nodulation genes. These fusions were prepared by insertion of the mini-μ-lac bacteriophage transposon MudI1734 (Castihlo et al. (1984) J. Bacteriol. 158:488–495) into the 14 kb HindIII fragment of ANUS43 (Innes et al. (1985) Mol. Gen. Genet. 201:426–432). This transposon contains the complete $E.\ coli$ lac operon minus the first two codons of lacZ and the upstream promoter region. MudIt734 is defective for phage growth and intracellular transposition and contains a kanamycin resistance gene ($Kan^R$). Expression of the lacZ gene encoding β-galactosidase from insertions of MudI1734 into foreign DNA should be dependent upon promoters upstream of the 5' lac operon end of the transposon. Regulation of expression of the lacZ gene will reflect regulation of the promoter region after which it is inserted. The use of Mud-lac bacteriophage for studies of gene regulation has been described previously (Casadaban and Cohen (1979) Proc. Natl. Acad. Sci. USA 76:4530–4533).

The 14 kb HindIII fragment containing the $R.\ trifolii$ nodulation gene has previously been cloned into a broad host range vector pKt240 (Schofield et al. 1984). The resultant derivative of pKt240 was designated pRt032. Insertions of MudI1734 (FIG. 1) into pRt032 were obtained by conjugal transfer of pRt032 into an $E.\ coli$ strain POI1734d carrying MudI1734 and a helper Mucts in its chromosome (Castihlo et al. 1984). Mucts was required because MudI1734 lacks the MuA and B gene necessary for transposition. Insertions of the transposon into pRt032 were selected, the pRtO32:MudI1734 insertions were transferred into $R.\ trifolii$ (pSym⁻) ANUS45 (Schofield et al. (1983) Mol. Gen. Genet. 192:459–465) and the ANU845 (pRtO32:MudI1734) transconjugants were assayed for nodulation phenotype on clover.

The location and orientation of 33 Mud-lac insertion mutants within the 14 kb nodulation region are shown in FIG. 1. The nodulation phenotype resulting from MudI1734 insertions was dependent on the site of insertion and correlated exactly with previous Tn5 insertions (Djordjevic et al. 1985). In addition to the three regions previously identified (supra), a fourth (IV, FIG. 1) was identified from an analysis of the mud-lac insertions. A fifth region (V, FIG. 1) was also identified by functional analysis of the DNA subfragment of the 14kb HindIII nod region (Rolfe et al., 1985). Mutants in regions IV and V caused a consistent two to five day delay in nodulation on clover, but only at light intensities above 400 μE/m². These mutants also induced shortened and thickened lateral roots on clover, compared to uninoculated clover or clover inoculated with wild type $R.\ trifolii$ ANU843.

DNA Sequence of the $R.\ trifolii$ nodulation genes

A 3.7 kb restriction fragment of the 14 kb HindIII fragment of $R.\ trifolii$ sym plasmid DNA was sequenced by the chain termination method (Sanger et al. (1977) Proc. Natl. Acad. Sci. USA 74:5463–5476). The nucleotide sequence of this 3668-bp fragment is presented in FIG. 2. Six open reading frames (ORF) are identified in this sequence; the direction of transcription of each ORF is shogun in FIG. 1. The predicted amino acid sequence of the gene products of these ORF's are given in FIG. 2. The six ORF's have been designated nodA-F (FIG. 2). Location of these nodulation genes within the 14 kb HindIII fragment is shown in FIG. 1. The sequence of FIG. 2 includes the full coding region of nodD, nodA, nodB and nodF as well as the partial coding region of nodC and nodE. The presence of overlapping nodA-nodB and nodF-nodE genes, and the close proximity of nodB and nodC, suggest that these genes compose two operons nodABC and nodFE which are coordinately transcribed. The presence of a terminator structure (Rosenberg and Court 1979) at the 3' end of nodD is consistent with separate transcription of nodD and nodFE.

The sequenced 3.7 kb fragment (FIG. 2) also contains the untranslated regions between nodD and nodA, and between nodD and nodF. The sequence between nodD and nodA is likely to contain promoter sequences that control transcription of nodD and nodABC, while the sequence between nodD and nodF is likely to contain promoter sequences for nodFE.

An important result of a comparison of the nucleotide sequence of the two untranslated regions was the discovery of conserved sequence elements, the first located between nucleotides 1756 and 1830 (FIG. 2) and the second between nucleotides 3076 and 3151. The conserved sequence elements (78% homologous) are aligned in FIG. 4. The two sequence elements are located, respectively, in the presumptive promoter regions of nodABC and nodFE. An analogous sequence was identified in the promoter region of $R\ meliloti$ nodABC genes (Torok et al., 1984, and Egelhoff et al., 1985). As shown in FIG. 4, the three reiterations of this sequence share 59% homology among all copies. By comparing the three sequences a core sequence element of 27 bp is identified. The 27 bp element of $R.\ trifolii$ nodABC is identical in sequence to the 27 bp element of $R.\ meliloti$. There are only two mismatches between $R.\ trifolii$ elements of nodABC and nodFE.

A 557 bp PstI fragment covering positions 2785 to 3342 (FIG. 2) containing the element of the nodFE promoter of $R.\ trifolii$ was used as a hybridization probe in Southern analysis (Hames and Higgins (eds.) 1985) in order to identify other reiterations of this element in the 14 kb HindIII fragment. Two other restriction fragments of the 14 kb nodulation region hybridized to the PstI probe. One of the restriction fragments contains the element of the nodABC promoter, the second fragment is localized in region V. The location of this region V fragment is shown in FIG. 1 and is outside of the 3.7 kb region sequenced.

DNA Sequence of Nodulation Gene Promoters of Bradyrhizobium sp. (Parasponia)

Bradyrhizobium sp. (Parasponia) strain ANU289 is a promiscuous, slow-growing rhizobia that infects Parasponia as well as a number of tropical egumes. The 14 kb HindIII fragment of $R.\ trifolii$ (described supra) was used as a hybridization probe of a genomic library of ANU289 DNA constructed in the λ-phage vector Charon 28. A 7.2 kb EcoRI sub-fragment of the 14 kb fragment known to contain the common nod genes (nodABCD) was also used as a probe. Homology with the nod genes of $R.\ trifolii$ was localized to two contiguous BamHi fragments of ANU289 DNA. This nod region of Bradyrhizobium sp. (Parasponia) ANU289 functionally complements nodulation deficient mutants of R. trifolii.

The 5.3 kb HindIII fragment of ANU289 DNA was sequenced by the chain termination technique. Analysis of this sequence revealed 5 open reading frames (ORF) greater than 400 codons in length. Comparative analysis of the translation products of these open reading frames with available sequence data from the fast-growing rhizobia has enabled the assignment of gene identity to 4 of the open reading frames. This fragment carries the entire coding region of nodA, nodB and nodD genes. In addition the fragment encodes the N-terminal 153 codons of nodC. NodA, B and C are closely linked and oriented in the same direction, while nodD is located 862 bp 5' to the initiation codon of nodA and is divergent from the nodABC cluster. The organization of the common nod genes of Bradyrhizobium sp. (Parasponia) is similar to organization in fast-growing rhizobia. The assignment of the initiation points of these genes is based on homology with the analogous genes in the fast-growing rhizobia. In addition to the four common nod genes, this nodulation locus contains a novel open reading frame located 5' to the nodABC genes, which is designated nodK. This reading frame is located within a 700 bp insertion of DNA between the nodD gene and the nodABC cluster, which is not present in this location in the fast-growing rhizobia. Preliminary hybridization data, however, indicate that nodK has structural homologues in R. meliloti, R. trifolii and R. leguminosarum DNA. In Bradyrhizobium sp. (Parasponia) nodK is believed to be coordinately transcribed with nodA, B and C.

An examination of the untranslated regions of the DNA sequence between nodD and the nodKABC operon (FIG. 3) reveals a sequence significantly homologous to the 27 bp sequence element identified in R. trifolii and R. meliloti. FIG. 4 provides a comparison of the promoter regulatory conserved sequence from R. trifolii nodABC and nodFE as well as R. meliloti nodABC and Bradyrhizobium sp. (Parasponia) nodKABC. A comparison of these four sequences provides a consensus sequence representing the average sequence in this area for all four reiterations of conserved sequence.

The consensus sequence shows no degeneracy in several significant portions. These portions are identical in all reiterations and represent the structure that is associated with the common function of the promoters, stimulation of expression by chemical factors in legume exudate.

Regulation of nod Gene Expression

Representative Mud-lac insertions from throughout regions I–IV were chosen for analysis of β-galactosidase activity (FIG. 1). Endogenous β-galactosidase activity was first assayed in free-living R. trifolii mutants grown in standard laboratory medium (TY medium, Berringer 1974) using the o-nitrophenyl-β-D-galactoside cleavage assay of Miller, 1972. As shown in Table 1, all insertion mutants produced β-galactosidase at low levels that were nevertheless above those in the parent strain ANU845 containing the plasmid pRt032, even when the orientation of the lacZYA genes was opposite to the known orientation of the target genes. The background level of β-galactosidase (taken as 150 units) is likely caused by promoters in the vector or promoter-like sequences in MudI1734, that are recognized by the Rhizobium transcriptional system.

TABLE 1

β-galactosidase activity of MudI1734 insertion mutants grown in TY[a]

| Insertion number | Gene or region interrupted | Orientation of lac relative to map in FIG. 1 | Units of β-galactosidase[b] |
|---|---|---|---|
| ANU845 (pRt032) | no insertion | N/A | 4.8 ± 1.3 |
| 545 | nodD | left to right | 815 ± 209 |
| 932 | nodD | left to right | 829 ± 275 |
| 520 | nodD | right to left | 60 ± 10 |
| 1003 | nodD | right to left | 70 ± 17 |
| 121 | nodA | right to left | 318 ± 69 |
| 218 | nodA | right to left | 146 ± 28 |
| 935 | nodA | right to left | 165 ± 46 |
| 346 | nodB | right to left | 98 ± 21 |
| 802 | nodC | left to right | 142 ± 23 |
| 839 | nodC | left to right | 68 ± 25 |
| 614 | region II | left to right | 179 ± 28 |
| 513 | region II | left to right | 110 ± 7 |
| 223 | region II | right to left | 136 ± 36 |
| 711 | region II | right to left | 155 ± 24 |
| 508 | region III | left to right | 150 ± 19 |
| 1027 | region III | left to right | 118 ± 24 |
| 936 | region III | right to left | 95 ± 16 |
| 806 | region III | right to left | 115 ± 26 |
| 810 | region IV | left to right | 220 ± 50 |
| 822 | region IV | left to right | 112 ± 25 |
| 1010 | region IV | right to left | 94 ± 8 |

[a]Insertions were in the R. trifolii ANU Nod region carried in pRt032 as a 14kb HindIII fragment. The location and orientation of insertions are given in FIG. 1. The MudI1734 insertion containing plasmids was present in ANU845, a pSym$^-$ derivative of ANU843.
[b]Units were determined according to Miller (1972) using the formula: units = 1000 × (OD$_{420}$ − 1.33 × OD$_{550}$)/(time × volume × OD$_{600}$). Each value represents the mean ± standard deviation of 3–6 separate assays when OD$_{600}$ was between 0.2 and 0.8.

Lac-fusions to nodD in the correct orientation, insertions 932 and 545 (FIG. 1), produced high levels of β-galactosidase in all growth phases in TY medium. This result indicates that nodD is constitutively expressed in the free-living R. trifolii. By comparison to nodD, the other nod genes did not appear to be highly expressed in the free-living state.

Nod gene expression could be qualitatively assayed by plating lawns of R. trifolii ANU845 cells containing the nod-lac fusions on nitrogen-free agar plates containing 5-bromo-4-chloro-3-indolyl-β-D-galactoside (X-gal), which produces a blue coloration on cleavage by β-galactosidase. The production of a blue color after plating on X-gal plates indicates expression of the lac-fusion.

An important result of the present work was the finding that certain nod:lac fusions were induced by the presence of clover roots. For example, bacterial lawns of R. trifolii ANU843 containing a nodA:lac fusion (mutant 121, FIG. 1) plated on X-gal and placed in contact with clover seedling roots produced intense blue areas at the site of bacterial contact with the seedling. Control plates lacking either seedling roots or bacteria produced no blue color. Similar induction of mutant 121 was observed with seedling roots of pea, bean, soybean and alfalfa (Table 2). In contrast, seedlings of non-legumes including maize, rice and Parasponia did not induce nodA:lac mutant 121. The absence of induction by Parasponia is interesting, since this non-legume is nodulated by Bradyrhizobium sp. (Parasponia), which contains the plant exudate-inducible promoter consensus sequence. The absence of induction by Parasponia may be a demonstration of the different mechanisms of nodulation in legumes and non-legumes.

TABLE 2

Induction of R. trifolii nodA-lac gene fusions by various plant exudates[1]

| Source of Exudate | Method of Assay[2] | |
|---|---|---|
| | X-Gal | ONPG |
| Legumes: | | |
| White clover | + | + |
| Red clover | + | ND |
| Subterranean clover | + | + |
| Alfalfa | + | + |
| Garden pea | + | + |
| Pea var. Rondo | + | ND |
| Afghanistan pea | + | ND |
| Soybean var. Bragg | + | + |
| Soybean var. Williams | + | + |
| Broad bean | + | + |
| French bean | + | ND |
| Lupine | + | + |
| Siratro | + | + |
| Desmodium | + | ND |
| Non-legumes: | | |
| Parasponia | − | ND |
| Corn | − | − |
| Wheat | − | − |
| Rice | − | ND |
| Bluegrass var. Kentucky | − | ND |
| Spinach | − | − |
| Cucumber | − | − |
| Brussels sprout | − | − |
| Carrot | − | − |

[1] Some of the results presented in this table appeared in Innes et al. 1985.
[2] A "+" sign indicates nod gene induction; a "−" sign indicates no induction of nod gene; "ND" indicates that the particular assay was not done. β-galactosidase assays were performed by placing plant seedlings or seedling growth medium in contact with lawns or liquid cultures of R. trifolii containing pRt032::121 or pRt032::218 in the presence of the indicated chromogenic substrate. The control strain used in these experiments was R. trifolii containing pRt032::802 which is a Mud-lac insertion in the antisense orientation in the nodC gene. (See FIG. 1).

Induction of several nod genes was quantitatively assayed, as β-galactosidase activity (Table 3) of mud-lac insertion mutants. Exponential growing cultures of various insertion mutants of R. trifolii were placed in contact with white clover roots; 1–4 hours later β-galactosidase activity was assayed. As shown in Table 3, insertions in the correct orientation in nodA and B were induced in the presence of plant root. Region II, region III and region IV also appear to be induced by plant exudate. Translational fusions constructed in nod region V were also found to be induced by legume exudate. In contrast, nodD expression was not affected by exposure to plant roots. All nod genes except nodD were induced 5–10 fold in the presence of clover. These results are consistent with induction of several nodulation related genetic operons by legume exudates. The direction of transcription of nodulation genes predicted from the results of Table 3 are consistent with that predicted by sequence data (FIG. 2).

TABLE 3

β-galactosidase activity of MudI1734 insertion mutants grown in TM in the absence and presence of white clover.

| Insertion[a] number | Gene or region interrupted | Orientation of lac relative to map in FIG. I | Units of activity[b] | |
|---|---|---|---|---|
| | | | −clover | +clover |
| 545 | nodD | left to right | 430[c] | 430 |
| 932 | nodD | left to right | 360 | 390 |
| 121 | nodA | right to left | 270 | 1700 |
| 935 | nodA | right to left | 130 | 1100 |
| 346 | nodB | right to left | 70 | 900 |
| 802 | nodC | left to right | 66 | 50 |
| 929 | region II | left to right | 55 | 40 |
| 513 | region II | left to right | 40 | 40 |
| 614 | region II | left to right | 100 | 110 |
| 223 | region II | right to left | 80 | 670 |
| 1027 | region III | left to right | 120 | 600 |
| 806 | region III | right to left | 50 | 50 |
| 810 | region IV | left to right | 100 | 1520 |
| 822 | region IV | left to right | 60 | 250 |
| 1010 | region IV | right to left | 50 | 50 |

[a] Location and orientation of insertions are given in FIG. 1.
[b] Units were determined according to Miller (1972) using the formula: units $= 1000 \times (OD_{240} - 1.33 \times OD_{550})/(\text{time} \times \text{volume} \times OD_{600})$
[c] When cells were grown in TM medium, β-galactosidase activity was lower than when grown in TY (see Table 2).

The level of lac expression from a promoter is only a minimal measure of the transcription initiated at that promoter. Further, different levels of lac expression can result from different fusions to the same promoter (Casadaban and Cohen, 1979). Such variations could be caused by RNA secondary structure, and stability and the presence and strength of opposing promoters (Shapira et al. (1983) Gene 25:71–82).

Recently, reports on the regulation of the common nod genes of R. meliloti (Mulligan and Long (1985) Proc. Natl. Acad. Sci. USA 82:6609–6613) and R. leguminosarum (Rossen et al. (1985) EMBO J. 4:3369–3373; Shearman et al. (1986) EMBO J. 5:647–652) confirm the results of the present work. Mulligan and Long (1985) report that nodC is expressed at very low levels in free-living R. meliloti but is induced in the presence of plant exudate. Rossen et al. 1985 report that nodC of R. leguminosarum is induced in the presence of plant exudates. Shearman et al. (1986) report that nodF of R. leguminosarum is induced by plant exudates. In each study, nodD expression is reported to be constitutive and not to be inducible by legume exudates.

The highly conserved promoter sequence element described above and in FIG. 4 precedes the R. trifolii nodABC, nodFE and the R. meliloti nodABC genes, all of which are subject to induction by legume exudates. An additional reiteration of the conserved sequence has been localized to nodulation region V of R. trifolii. Region V also contains gene(s) that are induced by legume exudate. The presence of the conserved sequence in these locations is consistent with its involvement in regulation of legume-activated expression of Rhizobium nod genes. The conserved regulatory sequences may not be found in all nodulation genes that are inducible by legume exudate. No reiteration of the sequence has yet been localized to R. trifolii region IV gene promoters.

The similarities in nod gene structure and, more importantly, similarities in the relative orientation and organization of nod genes in Bradyrhizobium sp. (Parasponia) and Rhizobium strains strongly suggests analogous gene regulation. Recent reports that B. japonicum also contains nodulation genes analogous to the "common" nod genes of the fast-growing rhizobia also suggest that a similar regulatory mechanism of the nodABC and D genes may obtain in both fast and slow growing rhizobia. In further confirmation of the universality of the iterations of the regulatory sequence, the consensus sequence of FIG. 4 has been identified in *B. japonicum* strains USDA 123 and USDA 110.

In *R. meliloti* and *R. leguminosarum* nodD is reported to be necessary in addition to plant factors for expression of the nodABC genes (Downie et al. (1985) Mol. Gen. Genet. 198:255–262; Mulligan and Long, 1985; Rossen et al., 1985) More recently Shearman et al (1986) EMBO J 5:647–652 have reported that nodD is also required, in addition to plant factors, for induction of nodF. Similarly, in *R. trifolii* the nodABC genes are unable to confer root hair curling, that is prerequisite for nodulation, in the absence of the nodD gene (Schofield, Ph.D. Thesis (1984) Australian National University, Canberra). These results suggest that the nodD gene product has a regulatory function in fast growing rhizobia in the expression of several other nod genes. The mechanism by which nodD regulates the expression of other nod genes is not yet known, but may involve the initial interaction of nodD directly or indirectly with legume exudate factors followed by binding of an altered nodD to DNA sequences in the promoter regions of the legume exudate-inducible nod genes. It is also possible that nodD interacts at different sequences in the promoter regions than that sequence involved directly with the factors in legume exudate.

The conservation of nod gene organization and the presence of conserved regulatory sequences in the nodulation gene promoters of both fast- and slow-growing rhizobia, demonstrated herein with the Bradyrhizobium sp. (Parasponia) nod genes, indicates that the regulation of nod genes in both systems is similar. Some variation in regulation of expression is likely to exist, at least in regard to the role of nodD as evidenced by the differences in phenotypes of nodD mutations in different rhizobia. In both *R. trifolii* and *R. leguminosarum*, nodD is absolutely required for nodulation (Rossen et al. 1985; Schofield, 1984). NodD mutations in *R. meliloti* are termed "leaky" nod⁻ and induce delays in root hair curling and nodulation (Mulligan and Long, 1985). Two distinct nodD genes, nodD-r1 and nodD-r2, which are 70% homologous to each other, have been identified in *R. japonicum*, a promiscuous fast-growing rhizobium that nodulates Glycine max v. Peking (U.S. patent application Ser. No. 763,934, filed Aug. 7, 1985). These nodD genes also are functionally distinct, one nodD-r2 is required for nodulation on siratro and functionally complements nodD mutants in *R. trifolii*; the other, nodD-r1 results in delayed nodulation and reduced ability of nodules to fix nitrogen. In Bradyrhizobium sp. (Parasponia), nodD mutants are able to nodulate the tropical legume siratro and the non-legume Parasponia with no apparent difference from the wild-type strain. In *B. japonicum* USDA 110, nodD mutants are deficient in nodulation on soybean. In all cases, however, expression of nodABC genes is found to be necessary for nodulation.

Construction of Recombinant Vectors for Plant Inducible Expression of Cloned Foreign Structural Genes Once the plant exudate-inducible promoter regions of the nodulation genes have been isolated, sequenced and cloned, it is possible to delete the nodulation structural genes (DNA normally transcribed under the control of these promoters) and replace them with a structural gene isolated from an extraneous source. This heterologous structural gene is thus placed under the control of the nodulation gene promoters and can be expressed under conditions where the nodulation gene promoters activate expression. The legume exudate-inducible promoter/foreign structural gene combination or chimeric gene can then be inserted into a vector, followed by introduction of the vector into a strain of bacterium in which the nodulation gene promoter is active. Alternatively, the composite gene or chimeric gene which includes the foreign structural gene and the legume exudate-inducible promoter can be integrated into the chromosome of the host bacterium in order to maximize the stability of the trait conferred by the chimeric gene. The nodulation gene promoters described herein have been shown to be active (induce expression responsive to legume exudate) in strains of Rhizobium, Bradyrhizobium, Agrobacterium.

The foreign structural gene must be inserted in the correct position and orientation with respect to the promoter in order to obtain expression of the structural gene controlled by the promoter. The foreign structural gene must be inserted downstream of the promoter. A second aspect of correct positioning of the structural gene refers to the distance, in base pairs, between the functional elements of the promoter and the translation start site of the foreign structural gene. Substantial variation appears to exist between promoters with respect to this distance. Therefore the structural requirements in this regard are best described in functional terms. Optimal spacing can be achieved by experiments varying the length of this distance. As a first approximation, reasonable operability can be obtained when the distance between the promoter and the inserted foreign gene is similar to the distance between the promoter and the gene that it normally controls. An alternate construction that will lead to a fusion protein is the insertion of the foreign structural gene into an existing nodulation gene. Fusion protein expression is exemplified by the Mud-lac fusions described herein. An additional positioning requirement in the case of fusion protein constructions is that the structural gene must be inserted such that the coding sequence of the two genes are in the same reading frame (or in phase), a structural requirement that is well understood in the art.

There are a number of ways in which a legume exudate-inducible promoter/foreign structural gene can be constructed. Example 9 provides one route to such a chimeric gene by inserting a DNA fragment comprising the consensus sequence of a nod gene promoter region into a reporter plasmid carrying a lacZ gene. Since this construction does not carry nodD, which appears to be required for expression of several nod genes, a source of nodD gene product may be additionally required for expression.

An alternative construction for expression of foreign structural genes under the control of the nodulation promoters is an expression cassette, as in example 10. An expression cassette can be constructed, for example, by the removal of the appropriate regulatory regions, including nodD, from the rhizobial DNA, followed by their insertion into a vector to form a recombinant vector. This recombinant vector is constructed such that a unique cloning site is positioned downstream from the nodulation gene promoter. Foreign structural genes can then be inserted into this unique cloning site and thereby placed under the control of the nodulation gene promoter.

The regulatory sequence defined herein function in the expression of certain nod genes in response to induction by legume exudate and nodulation inducing factors. The exact mechanism by which this sequence functions is still obscure. The sequence may provide an activator binding site or may represent an altered promoter. As stated above, in some cases nodD gene product may also be required for expression. There may also be other DNA sequences and/or other factors as yet undescribed which are required for expression.

The novel DNA constructions, vectors and plasmids disclosed herein are useful for amplifying the quantity of foreign structural genes, for transferring such foreign genes to selected host bacterial strains, for generating new bacterial strains and as intermediates for the construction of vectors having one or more of the foregoing uses. Bacterial strains containing the novel constructions described herein are useful for expressing foreign structural genes under certain specific conditions (on contact with legume exudate). Examples of proteins that can be usefully expressed under such conditions include insect toxin protein of *Bacillus thuringiensis*, hydrogenase (found in some, but not all, rhizobial strains), metallothionein and prolactin. The foregoing list is not intended as limiting but merely as an exemplary of the broad range of possibilities for selective synthesis of proteins on contact with plant exudate or nodulation gene inducing factors. In general, the invention makes it possible to produce any protein that may be of use, selectively, as a product extracted from culture or in situ in the vicinity of plant roots. In the latter case, the protein could confer an advantage for the host plant or for the bacterium in contact with the plant.

The following examples are intended to illustrate the invention only and are not intended to limit the scope of the invention.

Example 1: The construction of pRt032 plasmid

A molecular linkage map of the nodulation and nitrogen fixation regions of the sym plasmid of *R. trifolii* strain ANU843 has been reported by Schofield et al. (1983) Mol. Gen. Genet. 192:459–465. Phenotype analysis of Tn5 insertion mutants (Scott et al. (1982) J. Mol. Appl. Genet. 1:315–326) was used to define the limits of the nodulation gene region to a 14 kb HindIII DNA fragment of the ANU843 sym plasmid (Schofield et al. (1984) Plant Mol. Biol. 3:3–11). This fragment had been cloned into the plasmid cloning vector pBR328 to yield a recombinant plasmid pRt587 using the methods of Schofield et al. 1983. The 14 kb fragment from pRt587 was subcloned into the incompatibility group Q (Inc Q) vector pKT240 (Bagdasarian et al. (1981) Gene 16:237–247) yielding the recombinant plasmid pRt032. The pRt032 vector was transformed into *E. coli* strain RR1. Plasmid pRt032 was thereafter mobilized into a Sym plasmid-cured strain of *R. trifolii* ANU843, designated strain ANU845 (Zurkowski and Lorkiewicz (1978) Genetics Res. 32:311–314; and Djordjevic et al. (1983) J. Bacteriol. 156:1035–1045). The *R. trifolii* ANUS45 (pRt032) transconjugants were found to nodulate clover. Thus, the genes encoded on the 14 kb fragment restored nodulation ability to a *R. trifolii* strain lacking the Sym plasmid.

The plasmids pRt032 and pRt587 were introduced into *E. coli* strain RR1.

Example 2: Insertion of MudI1734 into the *Rhizobium trifolii* nod region

To study nod gene regulation, transcriptional fusions of several *R. trifolii* nod genes to the *E. coli* lac operon were prepared using the mini-Mu-lac bacteriophage transposon MudI1734 (Castihlo et al. (1984) J. Bacteriol. 158:488–495). The preparation of Mud-lac insertions into the *R. trifolii* nod region has been described in Innes et al. (1985) Mol. Gen. Genet. 201:426–432. The transposon MudI1734 was inserted into the pRt032 plasmid which contains the 14 kb HindIII fragment encoding nodulation and host specificity determinants. To obtain these insertions the plasmid pRt032 was first conjugally transferred from *E. coli* HB101 to *E. coli* strain POI1734d (Castihlo et al., 1984) which carried MudI1734 as well as a helper Mucts in its chromosome. Transconjugants of *E. coli* strain POI1734d containing the plasmid pRt032 were selected by replica plating on LB supplemented with carbenicillin and kanamycin. The Mucts was present in the recipient of this cross because MudI1734 lacks the Mua and Mub genes and can transpose only when the a and b gene products are supplied in trans. Next, to select for pRt032 that contained insertions of MudI1734, purified *E. coli* strain POI1734 (pRt032) colonies were mated with *E. coli* strain PK1724 (Innes et al., 1985) on Luria Broth (LB) plates, followed by replica plating onto M9 supplemented with L-tryptophan, carbenicillin, kanamycin and streptomycin. To minimize the number of siblings obtained, no more than five colonies were picked for purification from any one patch. Purified *E. coli* PK1724 strains containing pRt032 with MudI1734 insertions were individually conjugated on TY plates with Sym plasmid deleted *R. trifolii* strain ANU845. ANU845 transconjugants were selected on TM supplemented with carbenicillin and kanamycin. Individual ANU845 transconjugants were screened on white clover and subterranean clover for alterations in nodulation phenotype normally conferred by pRt032 (Rolfe et al. (1980) Plant Science Letters 19:277–284). Strains with alterations were mated to *E. coli* HB101 to allow easy isolation of plasmid DNA.

*E. coli* strains were grown in LB or M9 minimal medium supplemented with 20 μg/ml L-tryptohhan (Miller, 1972). *R. trifolii* strains were grown in TY medium (Beringer (1974) J. Gen. Microbiol. 84:188–198) or a modified TM minimal medium as described in Innes et al., 1985. Antibiotics were added at 100 μg/ml for solid medium (1.5% agar) and 50 μg/ml for liquid culture.

Transfers of the plasmid pRt032 were accomplished by patch mating of donor and recipient strains as described in Djordjevic et al., 1983.

The location and orientation of the MudI1734 insertions were determined by restriction enzyme analysis using a combination of HindIII, EcoRI, BglII and BamHI in single and double digestions.

Mutagenesis of plasmid pRt032 by MudI1734 yielded 188 insertions. When tested in ANU845, 58 of these (30%) were found to be delayed or lacking in nodulation in either white clover, subterranean clover or both. The position and orientation of the insertions was determined in all 58 mutants. Twenty-one of these mutants had deletions in the 14 kb fragment, four appeared to be dimers or rearrangements of pRt032, and the remaining 33 were insertions scattered throughout the 14 kb nod region. The nodulation phenotype resulting from insert i on of MudI 1734 was dependent on the site of insertion and correlated exactly with that found previously by Tn5 insertions (Djordjevic et al. (1985) Mol. Gen. Genet. 200:263–271). The location and orientation of each of these insertions within the 14 kb fragment are shown in FIG. 1.

Example 3: β-galactosidase expression from MudI1734 transcriptional fusions in ANU 485 grown in standard laboratory media The transposon MudI1734 contains the complete *E. coli* lac operon minus the first two codons of the lacZ gene and the upstream promoter region. No transcriptional initiation site is present (Castihlo et al., 1984). Expression of the lacZ gene from insertions of MudI1734 into foreign DNA is dependent upon the presence of promoters upstream of the 5' lac operon end of the transposon.

Representative strains of R. trifolii ANU845 containing MudI1734 insertions in the 14 kb nodulation region of pRt032 were chosen for analysis of β-galactosidase expression. β-Galactosidase activity was assayed using the o-nitrophenyl-β-D-galactoside (ONPG) cleavage assay essentially as described in Miller, 1972. Bacteria were permeablized with toluene. The results of these analyses are listed in Table 2. All insertions produced β-galactosidase levels above that endogenously present in ANU845 containing pRt032. This was true even when the orientation of the lacZYA genes was opposite to the known orientation of the target gene. The background level of β-galactosidase activity in this system was thus taken as 150 units (Table 2). In only one case, Mud-lac fusions to nodD in the correct orientation (insertions 932 and 545, FIG. 1), high levels of β-galactosidase were produced in all growth phases of the bacterium and in both minimal and rich media. This result indicates that nodD is constitutively expressed in free-living Rhizobium.

Example 4: Expression of β-galactosidase in ANU845 grown in the presence of clover plants Clover seeds were sterilized and germinated as previously described in Rolfe et al., 1980. Day-old sprouts (approximately 10) were transferred to 25 mm diameter glass test tubes containing a stainless steel mesh screen (18 mesh) supported above 10 ml of TM liquid. The tubes were then subjected to the same temperature and light regime as used in the nodulation assays described in Rolfe et al., 1980. The clover roots were allowed to grow down into the media. After four days, 1 ml of mid-logarithmic phase (OD 600= 0.50–0.8) Rhizobium culture grown in TM was added. Samples (1.5 ml) were removed immediately and again 3 hours later for β-galactosidase assay. A set of control tubes were subjected to the same treatment simultaneously with experimental tubes, but no plants were added. The results of these assays are presented in Table 3. Several nod genes were demonstrated to be induced in the presence of legume exudate.

Example 5: Plate assay for induction of expression of nodulation gene β-galactosidase gene fusions The induction of nodulation gene expression can be assayed qualitatively on indicator plates containing the chromogenic substrate 5-bromo-4-chloro-3-indolyl-β-D-galactoside (X-gal).

Inoculum of R. trifolii Mud-lac insertion mutant strains (for example mutant 121, designated R. trifolii ANU845 (pRt032::121) which contains a nodA:lac fusion) were plated (about 0.3 ml of a 1×10$^8$ bacteria/ml culture) on nitrogen-free Fahroeus medium (Vincent, 1970, *A Manual for the Practical Study of Root-Nodule Bacteria*, I.B.P. Handbook No. 15, Blackwell, Oxford and Edinburgh). Alternatively, the bacterial culture-inoculum was added to soft agar overlays of nitrogen-free Fahraeus medium spread over agar plates of the same medium. In either case, X-gal was incorporated into the medium at 4 mg/ml. Axenically-grown seedlings or dissected seedlings, for example white clover seedlings, were placed onto the pre-inoculated plates. The plates were incubated at 29° C. in the dark for 18 hours to allow development of bacterial lawns after which the lawn was examined for production of blue coloration at the site of contact with the seedling. Controls included plates on which either the seedlings or the bacteria or both were omitted.

Alternatively, one can test the inductive response by placing filter paper impregnated with an inducing composition on the X-gal medium seeded with the appropriate bacteria and incubating as described above. Extracts, purified fractions and pure compounds can be tested in this manner. Rhizobial cells in liquid media may also be treated with nodulation gene inducers, added in effective amounts to the liquid medium. For example, 7,4' dihydroxyflavone at a concentration of 2–5 µM is effective if the induction of the nodABC operon of R. trifolii.

Example 6: Nucleotide sequence of the nod region of Rhizobium trifolii ANU 843

The 14 kb fragment of R. trifolii strain ANU 843. described supra, was used as a source of DNA for sequence analysis. The region sequenced is shown in FIG. 2 and overlaps nodD, nodA, nodB and parts of nodC and nodF. The region includes presumptive promoter regions of nodF, nodD and the nodABC(IJ) operon. As shown in FIG. 1, the region sequence is contained on a 3.7 kb EcoRI-BglII restriction fragment. The fragment was sequenced by the chain termination method (Sanger et al. (1977) Proc. Natl. Acad. Sci. USA 74:5463–5476), using M13 sequencing vectors (MP18 and MP19 in E. coli strain JM101) (Norrander et al. (1983) Gene 26:101–106). The DNA sequence was determined on both strands using overlapping fragments. The DNA sequence was compiled and analyzed using Seq and Analyseq programs (Staden (1984) Nucl. Acids Res. 12:551–567).

In addition to conventional M13 sequencing, chain termination sequencing from Tn5 into flanking Rhizobium DNA was utilized. A 17-mer oligonucleotide (3'-TTCATCGCAGGACTTGC-5') complementary to the sequence from nucleotide 15 to 32 in the arms of Tn5 (Auerswald et al. (1981) Cold Spring Harbor Symposium Quantitative Biology 45:107–113) was synthesized by the phosphoroamidite method (Beaucage and Caruthers (1981) Tetrahedron Letters 22:1859–1862). DNA fragments extending from HindIII sites within Tn5 to EcoRI, BamHI or BglII sites in flanking Rhizobium DNA were cloned into MP18 and detected by using gamma-[$^{32}$P]ATP-labeled Tn5 primer. Tn5 primer extended chain termination sequencing from a given insertion site allows DNA sequence to be determined on different strands in each direction, such that the terminal 10 bp of Tn5 could be seen. In each instance the two sequences could be aligned with respect to each other by virtue of the 9 bp duplication of host DNA generated by Tn5 insertion. This method may be used to determine the nucleotide sequence of regions of DNA that have been genetically probed by Tn5 mutagenesis or for rapidly determining the genetic location of random Tn5 mutants of other bacterial species if homogeneous genes have already been characterized.

The DNA sequence of the EcoRI/BglII nod gene fragment, 3668 bp long, is presented in FIG. 2. Several open reading frames (ORF) were identified by sequence analysis and the predicted amino acid sequence of the nod gene products is also provided in FIG. 2.

Example 7: Nucleotide sequence of the nod region of Bradyrhizobium sp. (Parasponia) ANU 289

A library of genomic DNA of Bradyrhizobium sp. (Parasponia) strain ANU289 was constructed in the λ-phage vector Charon 28 and maintained in *E. coli* strain LE392. The 14 kb HindIII fragment containing the nodulation genes of *R. trifolii* described supra was used as a hybridization probe of this library. Several clones which hybridized to this probe were identified, one of which, λPR289-4, was chosen for further analysis. The presence of sequence homology to the *R. trifolii* nod probe was confirmed by hybridization of various restriction enzyme digests of λPR289-4 with a 7.2 EcoRI subclone of the 14 kb HindIII fragment which contained the common nod genes. The 7.2 kilobase EcoRI fragment hybridized to several restriction fragments of λPR289-4 including 8.4 kb and 16.8 kb EcoRI fragments, a 5.3 kb BamHI fragment and a 7.0 kb SalI fragment. Further hybridization analysis with the 14 kb probe localized the homology to two contiguous BamHI fragments of λPR289-4.

To ascertain if the Bradyrhizobium sp. (Parasponia) encoded genes were functionally analagous to the *R. trifolii* nod genes, the 5.3 kb BamHI fragment described supra carrying most of the hybridizing region was cloned into the BglII site of the broad host range plasmid pRK290. The resultant construct, designated pPR289-11, was mated into several *R. trifolii* Tn5 nod⁻ mutants. The Bradyrhizobium sp. (Parasponia) DNA sequences were found to partially complement mutant strains ANU 851 and ANU 272, which contain Tn5 insertions in nodD. These data indicate that pPR289-11 contain sequences that are functionally analagous to the *R. trifolii* nodD gene. The 5.3 kb HindIII fragment from Bradyrhizobium sp. (Parasponia) was subcloned from λPR289-4 into the vector pBR328. The resultant recombinant plasmid λPR289-10, was mapped using several restriction endonucleases and was then subjected to DNA sequence analysis. The complete DNA sequence of a 4.0 kb region of DNA from this plasmid was obtained by chain termination sequence analysis of various restriction fragments that had been subcloned into appropriately cleaved M13 vectors MP18 and MP19. The recombinant plasmid λPR289-10, also designated pPR289-10, was introduced into *E. coli* RR1.

The DNA sequence of the conserved nodulation region in ANU 289 is shown in FIG. 3. Computer analysis of this sequence reveals 5 open reading frames (ORF's) which are greater than 400 codons in length. Comparison of the available sequence data from fast-growing Rhizobium strains has enabled the assignment of gene identity to four of these open reading frames. The fragment sequenced carries the entire coding region of the nodA, nodB and nodD genes. In addition, the fragment codes the N-terminal 153 codons of nodC. As has been shown in fast-growing rhizobia, nodA, B and C are closely linked and oriented in the same direction, while nodD is located 862 bp 5' to the initiation codon of nodA. The assignment of the initiation points of these genes is based on homology with analagous genes in the fast-growing rhizobia. The DNA sequence of FIG. 3 also contains the untranslated region between the initiation sites of nodA and nodD, which presumably contains the promoter regions for both nodA and nodD. Examination of the sequence in this region reveals a sequence highly homologous with the reiterated sequence preceding the nodABC and nodFE genes of *R. trifolii*. This indicates that expression of nodKABC cluster of Bradyrhizobium sp. (Parasponia) will be regulated by legume exudate in a manner similar to that observed for nod genes of fast growing rhizobia.

Example 8: Detection of reiterated regulatory sequences in the 14kb HindIII nodulation region of the *R. trifolii* Sym plasmid A 557 bp PstI DNA fragment, including the sequence positions 2785–3342 of FIG. 2 and containing the legume exudate-inducible promoter element that precedes the nodFE genes of *R. trifolii* was isolated after restriction of the 14 kb HindIII *R. trifolii* nodulation region. This fragment was radioactively labeled by nick translation (Rigby et al. (1977) J. Mol. Bio. 113:237–251) for use as a probe in hybridization experiments.

Various restriction digests of pRt587 DNA were subjected to Southern blot analysis using this labeled 557 bp probe. The restricted DNA was separated by agarose gel electrophoresis (Aaij, C. and Borst (1972) Biochem. Biophys. Acta 269:503–517; and Maniatis et al., 1982) and transferred to nitrocellulose filters (Lawn et al. (1978) Cell 15:1157–1174). The nitrocellulose filters containing the immobilized pRt587 DNA restriction digests were prehybridized for 2 hours at 35° C. in 3X SSC (0.45 M NaCl 0.045 M Na-citrate), 50 mM HEPES (pH 7.0) (N-2-hydroxyethylpiperazine-N'-2-ethanesulfonic acid) 0.1% (w/v) sodium dodecyl sulfate and 0.2% (w/v) each polyvinyl pyrolidone, ficoll, and bovine serum albamin (BSA), 20 μg/ml denatured and sheared herring sperm DNA and 20 μg/ml *E. coli* tRNA before addition of approximately $1\times10^6$ cpm of probe DNA/filter. Hybridization was carried out for 18–24 hours at 65° C. Filters were then washed in 2 x SSC and 0.1% sodium dodecyl sulfate at room temperature for two hours before exposing to X-ray film for conventional autoradiography at −70° C. for 1–3 days.

Three pRt587 fragments hybridized to the 557 bp PstI fragment. One was a fragment containing the exact sequence of the PstI fragment, containing the promoter element preceding nodFE. The second fragment carried the reiterated promoter element preceding the nodABC genes, that had already been identified by sequencing (Example 6). The third fragment carried a previously unidentified reiterated element. This third fragment was localized to Region V (FIG. 1) of the 14 kb HindIII nodulation region which contains at least one legume exudate-inducible nodulation gene.

It will be appreciated by those of ordinary skill in the art that the Southern blot hybridization analyses described herein can be applied to probe DNA from a variety of sources including plasmid DNA and genomic DNA, and that alternative restriction fragments containing the legume-inducible Rhizobium or Bradyrhizobium nodulation promoter sequences can be used as hybridization probes. Further, conventional methods of oligonucleotide synthesis (Beaucage and Caruthers (1981) Tet. Letters 22:1859–1862) can be employed to prepare ligonucleotide probes having all or part of the nucleotide sequence of the nodulation promoter elements of the present invention. Particularly useful oligonucleotide probes can be synthesized using the consensus sequence of FIG. 4. It will also be understood that the hybridization conditions of Southern blot analyses using synthetic oligonucleotide probes may require adjustment of the hybridization conditions. Such adjustment can be made by varying the temperature of the hybridization. Appropriate hybridization conditions can be determined using the methods described in Hames and Higgins (eds.) (1985) *Nucleic Acid Hybridisation,* IRL Press, Oxford, UK, or by use of appropriate positive and negative controls. Appropriate positive controls are any DNA fragments containing known nodulation gene promoters containing the consensus sequence of FIG. 4. An appropriate negative control is a DNA fragment containing a promoter known not to contain the consensus sequence, for example the promoter of a Rhizobium nif gene promoter. A 21-mer oligonucleotide having the sequence 5'-CTGGTAAAATCCATTGTTTCG-3' based on the Bradyrhizobium sp. (Parasponia) nod-gene promoter sequence (FIG. 4) was prepared and radioactively labeled as a probe in hybridization experiments. This probe was used to demonstrate that there was only one copy of the nod gene consensus sequence of FIG. 4 in the 30 kb of DNA surrounding the nodKABC genes of Bradyrhizobium sp. (Parasponia). A similar oligonucleotide probe has been used to identify iterations of the regulatory sequence in *B. japonicum*.

Example 9: Construction of a recombinant plasmid containing a foreign structural gene under the control of a legume-inducible promoter (Method I)

The starting material for this construction is the 557 bp PstI DNA fragment (see Example 8) containing the legume exudate-inducible promoter consensus sequence. The single stranded ends of this PstI fragment are filled in by use of bacteriophage T4 DNA polymerase and synthetic restriction site linkers are then blunt end ligated to the filled in ends of the promoter containing fragment. In this example, HindIII linkers are ligated to the end of the promoter fragment, the fragment is then treated with HindIII restriction endonuclease and the resultant HindIII fragment is isolated by gel electrophoresis. The HindIII fragment containing the promoter can now be cloned into HindIII restriction sites.

Reporter plasmids which contain assayable structural genes lacking promoter regions and containing cloning sites downstream (5') of the structural gene have previously been used to assay promoter activity (see Rosenberg et al. (1982) *Promoters: Structure and Function*, Rodriguez and Chamberlin (eds) Praeger Publishers, N.Y., p. 387–406).

The construction of one such reporter plasmid pMp30 has recently been described by Okker et al. (1984) Nature 312:304–306. This plasmid contains the complete structural lacZ gene of *E. coli* and translational start signals, but does not contain lacP and lacO regulatory sequences. The plasmid also contains a unique HindIII cloning site upstream (5') of lacZ.

The HindIII fragment containing the legume exudate-inducible promoter described above is cloned into the unique HindIII site of pMp30. Two orientations of insertion of the HindIII fragment can result. Since promoters are usually active in only one direction, it is presumed that only one orientation of insertion will be active. The active or correct orientation of the legume-inducible promoter with respect to the foreign structural gene will be the same orientation as that of promoter and nodulation gene in the sym plasmid. In any event, the resultant recombinant plasmid(s) can be assayed for legume-inducible expression of lacZ (β-galactosidase) either after transformation into an *E. coli* (lac⁻) strain or in Rhizobium or Bradyrhizobium strains. The pMp30 derived plasmid described above may not be maintained in Rhizobium or Bradyrhizobium; however, the promoter/foreign structural gene construction can be introduced into these strains by cointegration of the pMp30 derived recombinant plasmid, with a broad host range plasmid such as derivatives of pLAFR1 or pKT. These cointegrated broad host range plasmids are then transformed into Rhizobium or Bradyrhizobium strains for assay of legume-inducible expression of lacZ.

Example 10: Construction of a recombinant plasmid containing a foreign structural gene under the control of legume exudate-inducible promoter (Method II)

The starting material for this construction is a plasmid pRt246 containing a Tn5 insertion in pRt032 within the nodA-nodD intergenic region of *R. trifolii*. The Tn5 insertion has been localized between the promoter element of nodABC genes and the structural nodA gene at base 1640 (FIG. 2). The phenotype of *R. trifolii* containing pRt246 is essentially nod⁺, so the inserted Tn5 sequences do not appear to disrupt nod gene expression. The recombinant plasmid, designated pRt246, consisting of the Tn5 containing 14 kb HindIII nodulation gene fragment has been introduced into *E. coli* strain RR1. The sequence from Tn5 provides three XhoI sites. A SphI restriction site is located at position 3139 (FIG. 2) within the conserved promoter region preceding nodFE of *R. trifolii*.

Digestion of pRt246 with XhoI endonuclease followed by SphI endonuclease results in a 2.1 kb XhoI-SphI fragment which is isolated by gel electrophoresis. This fragment will contain approximately 500 bp of Tn5, and the complete nodD gene flanked by inverted copies of the promoter conserved sequences.

The XhoI-SpbI fragment is then ligated into a cloning vector, for example SalI, SphI restricted pUC18, to form a recombinant vector containing an expression cassette for legume exudate-inducible expression. This recombinant vector contains unique cloning sites 3' to the regulatory promoter of nodABC (EcoRi, KpnI, SmaI, BamHI and XhoI), and 5' to the regulatory promoter of nodFE. These sites can be used for the introduction of foreign structural genes under the control of the legume exudate-inducible nodulation gene promoter.

The expression cassette described herein can be excised from pUC18 and after addition of appropriate linkers, inserted into appropriate broad host range vectors such as derivates of pLAFR1 or pKT. Such vectors can be transformed and maintained in strains of Rhizobium, Bradyrhizobium, Agrobacterium.

Those skilled in the art will appreciate that the invention described herein and the analytical methods, and methods used to isolate, characterize and manipulate DNA specifically described are susceptible to variations and modifications other than as specifically described. It is to be understood that the invention includes all such variations and modifications which fall within its spirit and scope.

We claim:

1. A method for selectively expressing a gene comprising a legume exudate-inducible promoter and a foreign structural gene under the control of said promoter which comprises the steps of:

(a) placing said foreign structural gene under the control of said legume exudate-inducible promoter, thereby forming a legume exudate-inducible gene, and inserting said legume exudate-inducible gene into a recombinant DNA molecule comprising a nodD gene of a strain of Rhizobium;

(b) introducing said recombinant DNA molecule comprising said legume exudate-inducible gene and said nodD gene into a bacterial strain in which said promoter is active and said nodD gene is expressed;

(c) combining said bacterial strain containing said legume exudate-inducible gene with an amount of a nodulation gene inducing composition effective for induction of a legume exudate-inducible gene, said composition comprising a nodulation gene inducing factor; and (d) assaying said bacteria strain for expression of said foreign structural gene under the control of said legume exudate-inducible promoter, wherein said legume exudate-inducible promoter comprises a nucleotide sequence having the consensus sequence 5'. . . ATCCAYNNYGYRGATGNW-YKYKATCSAAWCAATCRATTTTACCARW-YYKNSRR . . . 3' where N is A or G or T or C

Y is C or T

R is A or G

W is A or T

K is G or T and

S is C or G.

2. A method as recited in claim 1 wherein said legume exudate-inducible promoter is a nodulation gene promoter.

3. A method as recited in claim 1 wherein said promoter is a promoter of nodABC genes of a strain of Rhizobium.

4. A method as recited in claim 1 wherein said legume exudate-inducible promoter is a promoter of nodFE genes of a strain of Rhizobium.

5. A method as recited in claim 1 wherein said legume exudate-inducible promoter comprises the nucleotide sequence: 5'-CGCATTCTCGATC CACGCTGTAGATGAT-TGCGATCCAAACAATCAATTTT ACCAATCTTTCG-GAGTGCTTATTAG-3'.

6. A method as recited in claim 1 wherein said legume exudate-inducible promoter comprises the nucleotide sequence: 5'-CTCATTCCTTCAT CCATACTGCGGAT-GCTTTCGATCCAATCAATCAATTT TACCAATCCT-TCGGCATGCTCCATAG-3'.

7. A method as recited in claim 1 wherein said legume exudate-inducible promoter comprises the nucleotide sequence: 5'-GCATGTGCGGCAT CCATATCGCAGAT-GATCGTTATCCAAACAATCAATTT TACCAATCTTG-CAGACTCCTATTAG-3'.

8. A method as recited in claim 1 wherein said nodulation inducing composition comprises legume exudate.

9. A method as recited in claim 8 wherein said legume exudate is exudate of a legume selected from the group consisting of clover, pea, bean, soybean, alfalfa and siratro.

10. A method as recited in claim 1 wherein said foreign structural gene is an insect toxin gene of Bacillus thuringiensis.

11. A recombinant DNA molecule which comprises a legume exudate-inducible promoter and a foreign structural gene under the control of said promoter, said promoter comprising a nucleotide sequence having the consensus sequence:

5'. . . ATCCAYNNYGYRGATGNWYKYKATC-SAAWCAATCRATTTTACCARWYYKNSRR . . . 3' where N is A or G or C or T

Y is C or T

R is A or G

W is A or T

K is G or T and

S is C or G.

12. The recombinant DNA molecule of claim 11 wherein said legume exudate-inducible promoter is a nodulation gene promoter.

13. The recombinant DNA molecule of claim 12 wherein said nodulation gene promoter is a nodulation gene promoter of Rhizobium trifolii.

14. The recombinant DNA molecule of claim 12 wherein said nodulation gene promoter is a nodulation gene promoter of a Bradyrhizobium species.

15. The recombinant DNA molecule of claim 14 wherein said nodulation gene promoter is a nodulation gene promoter of Bradyrhizobium sp. (Parasponia).

16. The recombinant DNA molecule of claim 14 wherein said nodulation gene promoter is the promoter of the Bradyrhizobium sp. (Parasponia) nodKABC operon.

17. The recombinant DNA molecule of claim 14 wherein said nodulation gene promoter is a promoter of a nodulation gene of Bradyrhizobium japonicum.

18. The recombinant DNA molecule of claim 11 wherein said nodulation gene promoter is a promoter of a nodulation gene selected from the group which consists of nodA, nodB, nodC, nodF, nodE, nodK and nodH.

19. The recombinant DNA molecule of claim 11 wherein said nucleotide sequence is 5'-CGCATTCTCGATC-CACGCTGTAGATGATTGCGAT CCAAACAAT-CAATTTTACCAATCTTTCGGAGTGCTTA TTAG-3'.

20. The recombinant DNA molecule of claim 11 wherein said nucleotide sequence is 5'-CTCATTCCTTCATCCAT-ACTGCGGATGCTTTCGA TCCAATCAATCAATTT-TACCAATCCTTCGGCATGCTC CATAG-3'.

21. The recombinant DNA molecule of claim 11 wherein said nucleotide sequence is 5'-GCATGTGCGGCATC-CATATCGCAGATGATCGTTA TCCAAACAAT-CAATTTTACCAATCTTGCAGACTCCTA TTAG-3'.

22. A method for selectively expressing a gene comprising a legume exudate-inducible nodulation gene promoter and a foreign structural gene under the control of said promoter which comprises the steps of:

a) placing said foreign structural gene under the control of said legume exudate-inducible nodulation gene promoter, which promoter is the promoter of the nodABC genes of Rhizobium trifolii, thereby forming a legume exudate-inducible gene, and inserting said legume exudate-inducible gene into a recombinant DNA molecule comprising a nodD gene of a strain of Rhizobium;

b) introducing said recombinant DNA molecule comprising said legume exudate-inducible gene and said nodD gene into a bacterial strain in which said promoter is active and said nodD gene is expressed;

c) combining said bacterial strain containing said legume exudate-inducible gene with an amount of a nodulation gene inducing composition effective for induction of a legume exudate-inducible gene, said composition comprising a nodulation gene inducing factor; and d) assaying said bacterial strain for expression of said foreign structural gene under the control of said legume exudate-inducible promoter, wherein said legume exudate-inducible promoter comprises a nucleotide sequence having the consensus sequence 5'. . . ATC-CAYNNYGYRGATGNWYKYKATCSAAW-CAATCRATTTTACCARWYYKNSRR . . . 3' where N is A or G or T or C

Y is C or T

R is A or G

W is A or T

K is G or T and

S is C or G.

23. A method for selectively expressing a gene comprising a legume exudate-inducible nodulation gene promoter and a foreign structural gene under the control of said promoter which comprises the steps of:

a) placing said foreign structural gene under the control of said legume exudate-inducible nodulation gene promoter, which promoter is a promoter of nodFE genes of Rhizobium trifolii, thereby forming a legume exudate-inducible gene, and inserting said legume exudate-inducible gene into a recombinant DNA molecule comprising a nodD gene of a strain of Rhizobium;

b) introducing said recombinant DNA molecule comprising said legume exudate-inducible gene and said nodD gene into a bacterial strain in which said promoter is active and said nodD gene is expressed;

c) combining said bacterial strain containing said legume exudate-inducible gene with an amount of a nodulation gene inducing composition effective for induction of a legume exudate-inducible gene, said composition comprising a nodulation gene inducing factor; and d) assaying said bacterial strain for expression of said foreign structural gene under the control of said legume exudate-inducible promoter, wherein said legume exudate-inducible promoter comprises a nucleotide sequence having the consensus sequence 5'... ATCCAYNNYGYRGATGNWYKYKATCSAAWCAATCRATTTTACCARWYYKNSRR ... 3' where N is A or G or T or C

Y is C or T

R is A or G

W is A or T

K is G or T and

S is C or G.

24. A recombinant DNA molecule which comprises a legume exudate-inducible nodulation gene promoter and a foreign structural gene under the control of said promoter, said promoter comprising a nucleotide sequence having the consensus sequence: 5'... ATCCAYNNYGYRGATGNWYKYKATCSAAWCAATCRATTTTACCARWYYKNSRR ... 3' where N is A or G or C or T

Y is C or T

R is A or G

W is A or T

K is G or T and

S is C or G, and wherein said promoter is selected from the group of operons consisting of nodABC and nodFE from *Rhizobium trifolii*.

* * * * *

UNITED STATES PATENT AND TRADEMARK OFFICE
CERTIFICATE OF CORRECTION

PATENT NO. : 5,484,718
DATED : January 16, 1996
INVENTOR(S) : Schofield et al.

Page 1 of 2

It is certified that error appears in the above-indentified patent and that said Letters Patent is hereby corrected as shown below:

Column 1: lines 45-46: "Cornel l" should read --Cornell--.

Column 3: line 19: "22:407-449;" should read --32:407-449;--.

Column 5: line 42: "(Panasponia)." should read --(Parasponia).--; line 46: "2919 )." should read --2919).--; line 60: "Chem" should read --Chem.--.

Column 6: line 16: "only so" should read --only, so--; line 32: "TTGACA-TATAAT" should read --TTGACA----TATAAT--; line 48: "YTGGCAYGTTGCW" should read --YTGGCAYG....TTGCW--.

Column 9: line 19: "ANUS43" should read --ANU843--; line 22: "MudIt 734" should read --MudI1734--; line 44: "ANUS45" should read --ANU845--.

Column 10: line 35: "1984" should read --1983--; line 61: "egumes." should read --legumes.--; line 65: "14 Kb fragment" should read --14 kb fragment,--.

Column 15: line 9: "1985) More" should read --1985). More--; line 9: "EMBO J" should read --EMBO J.--; line 10: "5:647-652 have" should read --5:647-652, have--; line 34: "nodD as" should read --nodD, as--.

Column 16: line 59: "function" should read --functions--.

UNITED STATES PATENT AND TRADEMARK OFFICE
CERTIFICATE OF CORRECTION

PATENT NO. : 5,484,718

DATED : January 16, 1996

INVENTOR(S) : Schofield et al.

It is certified that error appears in the above-indentified patent and that said Letters Patent is hereby corrected as shown below:

Column 17: line 49;
"ANUS45" should read --ANU845--.

Column 18: line 30: "L-tryptohhan" should read --L-tryptophan--; line 53: "insert i on of MudI1734" should read --insertion of MudI1734--.

Column 19: line 36: "0.50 - 0.8)" should read --0.5 - 0.8)--.

Column 20: line 17: "ANU 843." should read --ANU 843,--.

Column 21: line 51: "anal agous" should read --analagous--; line 63: "HindlII" should read --HindIII--.

Column 22: line 19: "albamin" should read --albumin--; line 47: "ligonucleotide" should read --oligonucleotide--.

Column 24: line 19: "XhoI - SpbI" should read --XhoI - SphI--;

Signed and Sealed this

Sixth Day of August, 1996

Attest:

BRUCE LEHMAN

Attesting Officer     Commissioner of Patents and Trademarks